United States Patent
Pan et al.

(10) Patent No.: US 11,117,987 B2
(45) Date of Patent: *Sep. 14, 2021

(54) HYDROXYARYL FUNCTIONALIZED POLYMERS

(71) Applicant: Bridgestone Corporation, Tokyo (JP)

(72) Inventors: Xiao-Dong Pan, Baytown, TX (US); Zengquan Qin, Nashville, TN (US); Yuan-Yong Yan, Copley, OH (US); Dennis R. Brumbaugh, North Canton, OH (US)

(73) Assignee: Bridgestone Corporation, Chuo-ku (JP)

( * ) Notice: Subject to any disclaimer, the term of this patent is extended or adjusted under 35 U.S.C. 154(b) by 108 days.

This patent is subject to a terminal disclaimer.

(21) Appl. No.: 16/297,690

(22) Filed: Mar. 10, 2019

(65) Prior Publication Data

US 2019/0322777 A1    Oct. 24, 2019

Related U.S. Application Data

(60) Division of application No. 14/523,903, filed on Oct. 26, 2014, now Pat. No. 10,227,425, which is a continuation of application No. 12/810,846, filed as application No. PCT/US2008/088384 on Dec. 28, 2008, now Pat. No. 8,871,871.

(60) Provisional application No. 61/017,278, filed on Dec. 28, 2007, provisional application No. 61/127,586, filed on May 14, 2008, provisional application No. 61/082,181, filed on Jul. 18, 2008, provisional application No. 61/110,107, filed on Oct. 31, 2008.

(51) Int. Cl.

| | |
|---|---|
| *C08F 36/06* | (2006.01) |
| *C08F 36/04* | (2006.01) |
| *C08F 212/14* | (2006.01) |
| *C08F 290/06* | (2006.01) |
| *C08F 290/14* | (2006.01) |
| *C08F 297/02* | (2006.01) |
| *C08F 297/04* | (2006.01) |
| *C08L 53/02* | (2006.01) |
| *C08K 3/013* | (2018.01) |
| *C08C 19/44* | (2006.01) |
| *C07D 339/08* | (2006.01) |
| *C08F 236/10* | (2006.01) |

(52) U.S. Cl.
CPC ............ *C08F 36/06* (2013.01); *C07D 339/08* (2013.01); *C08C 19/44* (2013.01); *C08F 36/04* (2013.01); *C08F 212/14* (2013.01); *C08F 290/06* (2013.01); *C08F 290/14* (2013.01); *C08F 297/02* (2013.01); *C08F 297/04* (2013.01); *C08K 3/013* (2018.01); *C08L 53/02* (2013.01); *C08F 236/10* (2013.01); *Y02P 20/55* (2015.11)

(58) Field of Classification Search
None
See application file for complete search history.

(56) References Cited

U.S. PATENT DOCUMENTS

| | | | | |
|---|---|---|---|---|
| 5,331,058 A * | 7/1994 | Shepherd | ................ | C08F 36/04 525/332.3 |
| 5,486,568 A * | 1/1996 | Bening | .................. | C08C 19/44 525/102 |
| 5,565,526 A * | 10/1996 | Schwindeman | ........ | C08C 19/44 502/156 |
| 5,708,092 A * | 1/1998 | Schwindeman | ........ | C08C 19/44 260/665 R |
| 5,922,810 A * | 7/1999 | Schwindeman | ........ | C08C 19/00 525/194 |
| 6,008,295 A * | 12/1999 | Takeichi | ............... | B60C 1/0016 524/423 |
| 6,558,805 B2 * | 5/2003 | Khadir | ................. | C08G 77/442 152/450 |
| 2001/0053838 A1 * | 12/2001 | Quirk | ........................ | C08F 8/00 526/335 |
| 2019/0233557 A1 * | 8/2019 | Pan | ........................ | C08C 19/44 |

FOREIGN PATENT DOCUMENTS

JP    63218705 A  *  9/1988

OTHER PUBLICATIONS

JP 63-218705 A,, Sep. 1988, Eng. Ab. (Year: 1988).*

* cited by examiner

*Primary Examiner* — Satya B Sastri

(74) *Attorney, Agent, or Firm* — Meredith E. Hooker; David G. Burleson

(57) ABSTRACT

Vulcanizates with desirable properties can be obtained from compounds incorporating polymers that include hydroxyl group-containing aryl functionalities. The functionalities can be incorporated by using any or all of appropriate initiators, monomers and optional terminating compounds. Such polymers exhibit excellent interactivity with both conventional and non-conventional fillers.

6 Claims, No Drawings

HYDROXYARYL FUNCTIONALIZED POLYMERS

CROSS-REFERENCE TO RELATED APPLICATIONS

This is a division of U.S. application Ser. No. 14/523,903, which was filed 26 Oct. 2014 and issued as U.S. Pat. No. 10,227,425 on 12 Mar. 2019, which is a continuation of U.S. application Ser. No. 12/810,846, which had a 371(c) completion (filing) date of 7 Jul. 2010 and now issued as U.S. Pat. No. 8,871,871 on 28 Oct. 2014, which was a national stage entry of intl. appl. PCT/US2008/088384, filed 28 Dec. 2008, which claimed the benefit of each of U.S. provisional appl. Nos. 61/017,278 filed 28 Dec. 2007, 61/127,586 filed 14 May 2008, 61/082,181 filed 18 Jul. 2008, and 61/110,107 filed 31 Oct. 2008.

BACKGROUND INFORMATION

Traction performance is one of the primary evaluation criteria for tire treads, and performance on wet surfaces such as snow and ice is an important factor in that evaluation.

Deformation of tread rubber induced by road surface asperities, rate of water drainage between the tread and road surface, and possible adhesive interactions at the interface between tread and road are some of the complex, interrelated factors that complicate the type of quantitative mechanistic understanding needed to formulate tread compounds. To further improve tire performance, those involved in tread design and manufacture continue to investigate the numerous factors that affect wet traction.

Rubber goods such as tire treads are made from elastomeric compositions that contain one or more reinforcing materials; see, e.g., *The Vanderbilt Rubber Handbook*, 13th ed. (1990), pp. 603-04. The first material commonly used as a filler was carbon black, which imparts good reinforcing properties and excellent wear resistance to rubber compositions. However, carbon black-containing formulations often suffer from increased rolling resistance which correlates with an increase in hysteresis and heat build-up during operation of the tire, properties which need to be minimized to increase motor vehicle fuel efficiency.

The increased hysteresis resulting from the use of carbon black can be somewhat counteracted by reducing the amount (i.e., volume) of and/or increasing the particle size of the carbon black particles, but the risks of deterioration in reinforcing properties and wear resistance limits the extent to which these routes can be pursued.

Over the last several decades, the use of amorphous silica and treated variants thereof, both alone and in combination with carbon black has grown significantly. Use of silica fillers can result in tires with reduced rolling resistance, increased traction on wet surfaces, and other enhanced properties.

Despite the outstanding performance of treads employing silica and carbon black as reinforcing fillers, ever-more demanding regulatory and performance demands have led to continued investigations of alternative fillers. Examples of such non-conventional fillers include aluminum hydroxide (see, e.g., U.S. Pat. Nos. 6,242,522 and 6,489,389 as well as H. Mouri et al., "Improved Tire Wet Traction Through the Use of Mineral Fillers," *Rubber Chem. and Tech.*, vol. 72, pp. 960-68 (1999)); metal oxides having very high densities (see U.S. Pat. No. 6,734,235); magnetizable particles such as iron oxide or strontium ferrite used in the manufacture of tire sidewalls (see U.S. Pat. No. 6,476,110); macroscopic (e.g., 10-5000 μm mean diameter) particles of hard minerals such as alumina, $CaCO_3$, and quartz (see U.S. Pat. No. 5,066,702); pumice containing $SiO_2$ (U.S. Publ. No. 2004/0242750 A1); sub-micron ZnO particles (see U.S. Pat. No. 6,972,307); and micron-scale $ZnSO_4$, $BaSO_4$ and/or $TiO_2$ (see U.S. Pat. No. 6,852,785). More often, potentially useful fillers are merely strung together in list format; see, e.g., U.S. Pat. Nos. 4,255,296 and 4,468,496. Other non conventional filler materials include clays and complex oxides.

Recently, replacing some or all of the more common types of particulate fillers with inorganic oxides such as ferric oxide, ferrous oxide, aluminum oxide, etc., has been shown to provide vulcanizates with superior wet traction properties; see, e.g., U.S. Publ. No. 2008/0161467).

Enhancing dispersion of reinforcing filler(s) throughout the elastomer(s) can improve processability and certain physical properties. Efforts in this regard include high temperature mixing in the presence of selectively reactive promoters, surface oxidation of compounding materials, surface grafting, and chemically modifying the polymer(s).

Chemical modification of polymers often occurs at a terminus. Terminal chemical modification can occur by reaction of a terminally active, i.e., living (i.e., anionically initiated) or pseudo-living, polymer with a functional terminating agent. Terminal modification also can be provided by means of a functional initiator, in isolation or in combination with functional termination. Functional initiators typically are organolithium compounds that additionally include other functionality, typically functionality that includes a nitrogen atom. Unfortunately, functional initiators generally have relatively poor solubility in hydrocarbon solvents of the type commonly used in anionic polymerizations and cannot maintain propagation of living ends as well as more common alkyllithium initiators such as butyllithium; both characteristics negatively impact polymerization rate and efficiency.

Polymers incorporating 3,4-dihydroxyphenylalanine (DOPA) have been synthesized for some time, often for adhesive applications; see, e.g., U.S. Pat. No. 4,908,404. Because these polymers can be costly and difficult to produce, so-called bulk polymers approximating their performance have been pursued; see Westwood et al., "Simplified Polymer Mimics of Cross-Linking Adhesive Proteins," *Macromolecules* 2007, 40, 3960-64. However, the de-protection step utilized by the foregoing approach cannot be used when the polymer contains ethylenic unsaturation.

SUMMARY

Vulcanizates with desirable properties can be obtained from compounds employing polymers that include hydroxyl group-containing aryl functionalities. Such polymers enhance interactivity with both conventional and non-conventional fillers.

In one aspect is provided a method of making a functional polymer that includes one or more types of polyene mer and at least one functionalizing unit which includes an aryl group having at least one directly bonded OR substituent where R is a hydrolyzable protecting group. In a solution that includes an initiating compound and one or more types of ethylenically unsaturated monomers which include at least one type of polyene, the initiating compound is allowed to anionically initiate polymerization of the monomers so as to provide a carbanionic polymer. Optionally, the carbanionic polymer can be reacted with a terminating compound. The functionalizing unit(s) result from (i.e., is/are radical(s)

of) at least one of the initiating compound, the monomer(s), and the optional terminating compound.

The method can include an additional reaction step in which the protecting R group is hydrolyzed so as to provide an aryl group having at least one directly bonded hydroxyl group. This additional step can be the reaction of the carbanionic polymer with a terminating compound(s).

The aryl group of the functionalizing unit can include at least two directly bonded OR groups. Also or alternatively, a functionalizing unit can include a second aryl group, particularly when the unit is derived from a terminating compound.

Initiating compounds that can provide the functionalizing unit include those having the general formula $$R^1ZQ\text{-}M \qquad (I)$$

where M is an alkali metal atom; $R^1$ is a substituted or unsubstituted aryl group having at least one $OR^2$ substituent group where each $R^2$ is an R group that also is nonreactive toward M; Z is a single bond or a substituted or unsubstituted alkylene (acyclic or cyclic) or arylene group; and Q is a group bonded to M through a C, N or Sn atom. The $R^1$ aryl group can include a single aromatic ring (phenyl group) or two or more fused aromatic rings. Initiation with this type of functional initiator can result in a macromolecule that includes at least one polymer chain having terminal functionality defined by the general formula $$\text{-}Q'ZR^3 \qquad (II)$$

or a functionalized polymer defined by the general formula $$\kappa\text{-}\pi\text{-}Q'ZR^3 \qquad (III)$$

where $R^3$ is a substituted or unsubstituted aryl group that includes at least one $OR^4$ substituent group (with $R^4$ being H or R); Z is defined as above; Q' is the radical of Q, i.e., the residue of an initiating moiety bonded to the polymer chain through a C, N or Sn atom; π is a polymer chain; and K is a hydrogen atom or a functional group-containing radical generated by reaction of the polymer with a terminating compound. Where more than one $OR^4$ group is present, each can be on the same or different rings and, in certain embodiments, at least two $OR^4$ substituents can be adjacent.

Where a functionalizing unit results from a monomer, the monomer can include an aryl group, preferably a phenyl group, that has at least one directly bonded OR group. The resulting polymer can include multiple mer resulting from incorporation of alkenes (A units) and at least three mer of the type just described (B units) which can be non-adjacent or can constitute a block within the polymer. If a block of B units is present, it can be relatively close to a terminus of the polymer, i.e., no more than six, four or two polymer chain atoms from a terminal unit. In other embodiments, one or more B units can be incorporated into the polymer, typically after polymerization of the other monomers has been accomplished, optionally followed by reaction with a compound which optionally can provide additional terminal functionality to the polymer. (This compound need not be of a type capable of providing the specific functionality shown below in formula (IV) and, instead, can provide any of a variety of functionalities including inter alia those containing one or more heteroatoms.)

Where a functionalizing unit results from reaction of the carbanionic polymer with a terminating compound, that functionality can have the general formula $$\begin{array}{c}-Q''Z'R^3\\|\\R^6\end{array} \qquad (IV)$$

where Z' is a single bond or an alkylene group; $R^3$ is defined as above; $R^6$ is H, a substituted or unsubstituted aryl group which optionally can include one or more $OR^4$ substituent groups, R', or JR' where J is O, S, or —NR' (with each R' independently being a substituted or unsubstituted alkyl group); and Q'' is the residue of a functionality that is reactive with carbanionic polymers but which itself is non-reactive toward such polymers. The $R^3$ aryl group can include a single aromatic ring (phenyl group) or two or more fused aromatic rings, and the $OR^4$ groups can be on the same or different rings of the aryl group although, in certain embodiments, the $OR^4$ substituents advantageously can be adjacent. Additionally, $R^6$ and a portion of $R^3$ can be linked so that, together with one or more atoms of the Q'' group to which they are bonded (and optionally Z'), they form a ring that is bound to or fused with the $R^3$ aryl group; examples include any of a variety of flavone- and anthrone-type structures which have one or more $OR^4$ substituent groups on at least one of the aryl groups. (This is described in more detail below in connection with formula (IVb).)

In a variation of the foregoing method, a similar functionalizing unit can result from reaction of a terminating compound of the type just described with other types of terminally reactive polymers, for example, a pseudo living polymer.

In certain embodiments, the polyene(s) can be conjugated dienes. In these and other embodiments, the polymer also can include vinyl aromatic mer which preferably are incorporated substantially randomly with the conjugated diene mer along the polymer chain.

In each of the foregoing, the polymer can be substantially linear. In certain embodiments, the substantially linear polymer can include as a terminal moiety the radical of a compound that includes at least one aryl group having one or more substituent groups that can be hydrolyzed to hydroxyl groups.

Compositions that include particulate fillers and polymers of the type described above also are provided, as are methods of providing and using such compositions. Also provided are vulcanizates made from such filled compositions. In any or all, the polymer can interact with particulate fillers including carbon black and silica as well as, advantageously, non-conventional fillers such as inorganic oxides and hydroxides, clays and the like.

Other aspects of the present invention will be apparent to the ordinarily skilled artisan from the description of various embodiments that follows. In that description, the following definitions apply throughout unless the surrounding text explicitly indicates a contrary intention:

"polymer" means the polymerization product of one or more monomers and is inclusive of homo-, co-, ter-, tetra-polymers, etc.;

"mer" or "mer unit" means that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetra-polymers, and the like;

"random interpolymer" means an interpolymer having mer units derived from each type of constituent monomer incorporated in an essentially non-repeating manner and being substantially free of blocks, i.e., segments of three or more of the same mer;

"reactive polymer" means a polymer having at least one site which, because of the presence of an associated catalyst or initiator, readily reacts with other molecules, with the term being inclusive of inter alia pseudo-living and carbanionic polymers;

"catalyst composition" is a general term encompasses a simple mixture of ingredients, a complex of various ingredients that is caused by physical or chemical forces of attraction, a chemical reaction product of some or all of the ingredients, or a combination of the foregoing, the result of which is a composition displaying catalytic activity with respect to one or more monomers of the appropriate type;

"gum Mooney viscosity" is the Mooney viscosity of an uncured polymer prior to addition of any filler(s);

"compound Mooney viscosity" is the Mooney viscosity of a composition that includes, inter alia, an uncured or partially cured polymer and particulate filler(s);

"substituted" means containing a heteroatom or functionality (e.g., hydrocarbyl group) that does not interfere with the intended purpose of the group in question;

"directly bonded" means covalently attached with no intervening atoms or groups;

"polyene" means a molecule with at least two double bonds located in the longest portion or chain thereof, and specifically is inclusive of dienes, trienes, and the like;

"polydiene" means a polymer that includes mer units from one or more dienes;

"phr" means parts by weight (pbw) per 100 pbw rubber;

"non-coordinating anion" means a sterically bulky anion that does not form coordinate bonds with the active center of a catalyst system due to steric hindrance;

"non-coordinating anion precursor" means a compound that is able to form a non-coordinating anion under reaction conditions;

"radical" means the portion of a molecule that remains after reacting with another molecule, regardless of whether any atoms are gained or lost as a result of the reaction;

"aryl group" means a phenyl group or a polycyclic aromatic radical;

"terminus" means an end of a polymeric chain; and

"terminal moiety" means a group or functionality located at a terminus.

Throughout this document, all values given in the form of percentages are weight percentages unless the surrounding text explicitly indicates a contrary intention. The relevant portions of any mentioned patent or patent publication is incorporated herein by reference.

DETAILED DESCRIPTION OF PREFERRED EMBODIMENTS

As apparent from the foregoing Summary, the method can involve any of a variety of possible permutations or combinations thereof, and the resulting polymer can be characterized in a variety of ways. Generally, the polymer includes mer derived from one or more polyenes, particularly dienes, and terminal functionality defined by either or both of formulas (II) and (IV) and/or one or more of the aforedescribed B mer units. In at least certain embodiments, the polymer also can include directly bonded pendent aromatic groups.

The following describes the production and use of a polymer that includes multiple A mer, i.e., alkene units; optionally, multiple C mer, i.e., units that include a pendent aryl group, particularly a phenyl group, and, where at least some of the desired functionalization is to be derived from functional monomers, at least one B mer, i.e., a unit that includes a pendent aryl, preferably phenyl, group with at least one directly bonded OR group. Each of the A, B and C mer can result from incorporation of ethylenically unsaturated monomers.

The A mer typically result from incorporation of polyenes, particularly trienes (e.g., myrcene) and dienes, particularly $C_4$-$C_{12}$ dienes and even more particularly conjugated dienes such as 1,3-butadiene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, isoprene, 4-methyl-1,3-pentadiene, 2,4-hexadiene, and the like. Some or all of the A mer can be derived from one or more types of dienes, particularly one or more types of conjugated dienes, e.g., 1,3-butadiene. In some embodiments, essentially all (i.e., at least 95%) of the polyenes can be dienes, particularly conjugated dienes.

Polyenes can incorporate into polymeric chains in more than one way. Especially for tire tread applications, controlling this manner of incorporation can be desirable. A polymer chain with an overall 1,2-microstructure, given as a numerical percentage based on total number of polyene units, of from ~10 to ~80%, optionally from ~25 to ~65%, can be desirable for certain end use applications. A polymer that has an overall 1,2-microstructure of no more than ~50%, preferably no more than ~45%, more preferably no more than ~40%, even more preferably no more than ~35%, and most preferably no more than ~30%, based on total polyene content, is considered to be substantially linear. For certain end use applications, keeping the content of 1,2-linkages even lower, e.g., to less than about 7%, less than 5%, less than 2%, or less than 1%, can be desirable.

Depending on the intended end use, one or more of the polymer chains can include pendent aromatic groups, which can be provided by C mer, i.e., mer derived from vinyl aromatics, particularly the $C_8$-$C_{20}$ vinyl aromatics such as, e.g., styrene, α-methyl styrene, p-methyl styrene, the vinyl toluenes, and the vinyl naphthalenes. When used in conjunction with one or more polyenes, C mer can constitute from ~1 to ~50%, from ~10 to ~45%, or from ~20 to ~40% of the polymer chain; random microstructure can provide particular benefit in some end use applications such as, e.g., rubber compositions used in the manufacture of tire treads. Where a block interpolymer is desired, C units can constitute from ~1 to ~90%, generally from ~2 to ~80%, commonly from ~3 to ~75%, and typically ~5 to ~70% of the polymer chain. (In this paragraph, all percentages are mole percentages.)

Exemplary interpolymers include those in which one or more conjugated dienes are used to provide the A units, i.e., polydienes; among these, 1,3-butadiene can be one of several or the only polydiene employed. Where C units are desired, they can be provided from styrene so as to provide, for example, SBR. In each of the foregoing types of exemplary interpolymers, one or more B units also can be incorporated.

B units include a pendent aryl group which includes one or more directly bonded hydroxyl groups. Because the H atoms of hydroxyl groups are active and can interfere with certain polymerization processes, the one or more B units typically are provided from compounds that include R groups, i.e., groups that are non-reactive in the types of conditions utilized when polymerizing ethylenically unsaturated monomers but which later can be removed, typically by hydrolysis or similar reaction, so as to provide the desired hydroxyl groups. The particular type(s) of protecting group(s) employed should not interfere with the polymerization process, and the de-protection process employed to provide hydroxyl groups should not destroy or otherwise react with ethylenic unsaturation in the polymer resulting from the presence of A units. A non-limiting class of useful protecting groups is trialkylsiloxy groups, which can be provided by reacting hydroxyl groups with a trialkylsilyl halide. While the following examples employ tert-butyldimethylsiloxyl groups, others such as acetal, tert-butyl ether, 2-methoxyethoxy ether, and the like also can be used.

The number of OR groups on the aryl, typically phenyl, group of each B unit need not be the same, where the number is the same, the OR groups need not be at the same position(s) on those rings. Using a phenyl group as a representative aryl group, relative to the point of attachment of the phenyl group to the polymer chain, a single OR group can be located ortho, meta, or para on the phenyl ring, while multiple OR groups can be provided 2,3-, 2,4-, 2,5-, 2,6-, 3,4-, 3,5-, 3,6-, 2,3,4-, 2,3,5-, etc., on the phenyl ring.

B units typically are provided from vinyl aromatic compounds that include one or more hydroxyl-producing groups directly attached to their aryl, typically phenyl, rings. Such compounds can be represented by the general formula $$CH_2=CHR^1 \qquad (V)$$

where $R^1$ is defined as above and which here can include from 1 to 5 inclusive OR groups with each R independently being the type of protecting group described above. (Although each R need not be identical, ease and simplicity typically result in a single type of R moiety being used in a given compound.) The OR groups can be substituents of the same ring of $R^1$ or can be substituents of different rings and, where $R^1$ contains three or more OR groups, two of them can be substituents of one ring with the other(s) being substituent(s) of other ring(s). In one embodiment, two OR groups can be at the 3 and 4 positions of the same ring within the aryl group, preferably a phenyl group. Where $R^1$ is other than a phenyl group and includes more than one OR group and where the OR groups are on more than one ring, at least two of the OR groups preferably are least somewhat proximate, i.e., directly bonded to ring C atoms that are separated by no more than 4, preferably 3, and even more preferably 2, other ring atoms. Many of these compounds advantageously are soluble in the types of organic solvents set forth below.

When one or more formula (V)-type compounds is polymerized, it/they provide the B unit(s), after which each of the R moieties can be hydrolyzed so as to provide phenolic hydroxyl groups.

The number of B units typically is small relative to the number of A units and, if present, C units; a relatively small number of B units has been found to provide a satisfactory level of desired properties, with further improvements in those properties not necessarily being proportional to the number of B units present. This relatively small number can be expressed in a number of ways. For example, the weight percentage of the final polymer attributable to B units commonly is less than 2%, more commonly from ~0.1 to ~1.5%, and typically from ~0.2 to ~1.0%. The percentage of B mer relative to the total number of mer in the polymer commonly is less than 1%, more commonly from ~0.01 to ~0.75%, and typically from ~0.05 to ~0.5%. The total number of B units in a given polymer generally is from 1 to several dozen, commonly from 1 to 12, more commonly from 1 to 10, and most commonly from 1 to 5.

The B units can be separated from one another, or two or more B units can be contiguous along the polymer chain. (While the ordinarily skilled artisan understands how to synthesize random and block interpolymers, each is discussed in some detail below.) Further, the B units can incorporated near the beginning of the polymerization, near the end of the polymerization, or at any one or more intermediate points; in the first two of the foregoing possibilities, a B unit can be provided within 6 chain atoms of, within 2 units of, adjacent to a terminus of the polymer, or as a terminal unit, either alone or as part of a block.

The foregoing types of polymers can be made by emulsion polymerization or solution polymerization, with the latter affording greater control with respect to such properties as randomness, microstructure, etc. Solution polymerizations have been performed for many decades, so the general aspects thereof are known to the ordinarily skilled artisan, so only certain general aspects are provided here for convenience of reference.

Both polar solvents, such as THF, and non-polar solvents can be employed in solution polymerizations, with the latter type being more common in industrial practice. Examples of non-polar solvents include various $C_5$-$C_{12}$ cyclic and acyclic alkanes as well as their alkylated derivatives, certain liquid aromatic compounds, and mixtures thereof. The ordinarily skilled artisan is aware of other useful solvent options and combinations.

Depending on the nature of the polymer desired, the particular conditions of the solution polymerization can vary significantly. In the discussion that follows, living polymerizations are described first followed by a description of pseudo-living polymerizations. After these descriptions, optional functionalization and processing of polymers so made are discussed.

Solution polymerization typically involves an initiator. Exemplary initiators include organolithium compounds, particularly alkyllithium compounds. Examples of organolithium initiators include N-lithio-hexamethyleneimine; n-butyllithium; tributyltin lithium; dialkylamino-lithium compounds such as dimethylaminolithium, diethylaminolithium, dipropylaminolithium, dibutylaminolithium and the like; dialkylaminoalkyllithium compounds such as diethylamino-propyllithium; and those trialkyl stanyl lithium compounds involving $C_1$-$C_{12}$, preferably $C_1$-$C_4$, alkyl groups.

Multifunctional initiators, i.e., initiators capable of forming polymers with more than one living end, also can be used. Examples of multifunctional initiators include, but are not limited to, 1,4-dilithiobutane, 1,10-dilithiodecane, 1,20-dilithioeicosane, 1,4-dilithiobenzene, 1,4-dilithionaphthalene, 1,10-dilithioanthracene, 1,2-dilithio-1,2-diphenylethane, 1,3,5-trilithio-pentane, 1,5,15-trilithioeicosane, 1,3,5-trilithiocyclohexane, 1,3,5,8-tetralithiodecane, 1,5,10,20-tetralithioeicosane, 1,2,4,6-tetralithiocyclohexane, and 4,4'-dilithiobiphenyl.

In addition to organolithium initiators, so-called functionalized initiators also can be useful. These become incorporated into the polymer chain, thus providing a functional group at the initiated end of the chain. Examples of such materials include lithiated aryl thioacetals (see, e.g., U.S. Pat. No. 7,153,919) and the reaction products of organolithium compounds and, for example, N-containing organic compounds such as substituted aldimines, ketimines, secondary amines, etc., optionally pre-reacted with a compound such as diisopropenyl benzene (see, e.g., U.S. Pat. Nos. 5,153,159 and 5,567,815). Use of a N atom-containing initiator such as, for example, lithiated HMI, can further enhance interactivity between the polymer chains and carbon black particles. Many of these functional initiators are poorly soluble in many of the solvents set forth above, particularly those solvents that are relatively non-polar.

In contradistinction, many compounds included in formula (I) exhibit acceptable solubility in the types of organic liquids commonly employed as solvents in solution polymerizations. Compounds included within this formula hereinafter are referred to as $R^1$-containing initiators.

The aryl group of the $R^1$-containing initiator can be a phenyl group or two or more fused aromatic rings. Where the $R^1$ aryl group includes more than one $OR^2$ group (with each $R^2$ being an R group that is nonreactive toward M), the $OR^2$ groups can be substituents of the same ring or of different rings within the aryl group; where the aryl group contains three or more $OR^2$ groups, two of them can be substituents of one ring with the other(s) being substituent(s) of other ring(s). In one embodiment, two $OR^2$ groups can be at the 3 and 4 positions of the same ring within the aryl group, preferably a phenyl group. Where $R^1$ is other than a phenyl group and includes more than one $OR^2$ group and where the $OR^2$ groups are on more than one ring, at least two of the $OR^2$ groups preferably are at least somewhat proximate, i.e., directly bonded to ring C atoms that are separated by no more than 4, preferably 3, and even more preferably 2, other ring atoms. Where a single $OR^2$ group is present on a phenyl group, it can be located at any ring position, although para from Z might be preferable for certain applications.

The $R^2$ moieties of the $R^1$-containing initiator ensure that no active hydrogen atoms are present in the $R^1$ aryl group. Such active hydrogen atoms would interfere with the ability of the $R^1$-containing initiator to anionically initiate polymerizations. Unless a particular $R^2$ moiety constitutes a group that is capable of providing interactivity with particulate filler, it preferably also is capable of being hydrolyzed to a hydrogen atom. Trialkylsiloxy groups are a non-limiting example of the type of group that can serve these dual purposes; such groups can be provided by reacting hydroxyl groups attached to the $R^1$ aryl group with a trialkylsilyl halide. Although each $R^2$ need not be identical, ease and simplicity typically result in a single type of $R^2$ moiety for a given $R^1$-containing initiator.

When the $R^1$-containing initiator initiates polymerization, its radical forms one end of a polymer chain (see formulas (II) and (III)). The $R^2$ moieties of this radical typically are hydrolyzed so as to provide hydroxyl substituents to the $R^3$ group of formulas (II) and (III). This type of $R^3$ group has been found to provide excellent interactivity with a wide variety of particulate fillers including carbon black and silica as well as non-conventional fillers such as inorganic oxides and hydroxides, clays and the like.

In the $R^1$-containing initiator, M is an alkali metal atom (preferably a K, Na or Li atom, most preferably a Li atom), and Q is a group bonded to M through a C, N or Sn atom. Generally, Q does not contain any active hydrogen atoms which, as appreciated by the ordinarily skilled artisan, interfere with the efficacy of the $R^1$-containing initiator. Potentially useful Q groups are too numerous for a comprehensive listing, but a few non-limiting examples can be provided; from these, the ordinarily skilled artisan can envision numerous other alternatives.

Thioacetals are one type of potentially useful Q group. These functionalities have the general formula

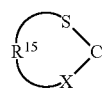

(VI)

where $R^{15}$ is a $C_2$-$C_{10}$ alkylene group, preferably a $C_2$-$C_8$ alkylene group, more preferably a $C_3$-$C_6$ group; X is selected from S, O and $NR^{16}$ wherein $R^{16}$ can be a $C_1$-$C_6$ trialkylsilyl group, a $C_1$-$C_{20}$ alkyl group, a $C_4$-$C_{20}$ cycloalkyl group, a $C_6$-$C_{20}$ aryl group with the proviso that any of the following can be attached: $C_1$-$C_{10}$ alkyl groups, $C_6$-$C_{20}$ aryl groups, $C_2$-$C_{10}$ alkenyl groups, $C_3$-$C_{10}$ non-terminal alkynyl groups, ethers, tert-amines, phosphines, sulfides, silyls, and mixtures thereof. One preferred species includes an S atom as X and a $C_3$ alkylene group as $R^{15}$, i.e., a 1,3-dithiane. In certain aspects, Q can be a group that includes a heteroatom-substituted cyclic moiety adapted to bond to an alkali metal atom, such as Li. For additional information, the interested reader is directed to U.S. Pat. No. 7,153,919.

Other potentially useful Q groups include $SnR^7_2$ where each $R^1$ independently is a hydrocarbyl (e.g., alkyl, cycloalkyl, aryl, aralkyl, alkaryl, etc.) group or, together, form a cycloalkyl group, and $NR^8$ where $R^8$ is a hydrocarbyl group, particularly an aryl, a $C_3$-$C_8$ cycloalkyl, or a $C_1$-$C_{20}$ alkyl group; included among the latter are cycloalkyleneiminoalkyllithium compounds such as those described in, for example, U.S. Pat. No. 5,574,109. Also potentially useful as Q groups are any of a variety of linear or branched alkyl groups, non-limiting examples of which include butyl, pentyl, hexyl, heptyl, octyl, etc. All the foregoing initiators can be prepared from hydroxyl-substituted benzaldehydes through synthesis techniques described in more detail in the examples that follow.

Compounds defined by formula (I) can be provided in a variety of ways, with the choice of synthetic route depending to a large extent on particular nature of Q. For example, a compound with multiple hydroxyl groups attached to an aryl group and at least one other functionality can react, through the other functionality, with a compound so as to provide a Q group; thereafter, the H atom(s) of the hydroxyl group(s) can be reacted with a compound that can provide the aforementioned $R^2$ groups, and the resulting material can be reacted with an alkali metal-containing material, e.g., an organolithium. This type of synthetic approach is employed below in the examples to provide an exemplary dithiane-type initiator.

The $R^1$-containing initiator can be made external to the polymerization vessel where it is to act as an initiator. In this case, a blend of monomer(s) and solvent can be charged to the reaction vessel, followed by addition of initiator, which often is added as part of a solution or blend (i.e., in a solvent carrier). For reasons of convenience, the $R^1$-containing initiator typically is synthesized in situ.

Although the ordinarily skilled artisan understands the conditions typically employed in solution polymerization, a representative description is provided for ease of reference. The following is based on a batch process, although the ordinarily skilled artisan can adapt this description to, semi-batch, continuous, or other processes.

Solution polymerization typically begins by charging a blend of monomer(s) and solvent to a suitable reaction vessel, followed by addition of a coordinator (if used) and initiator, which often are added as part of a solution or blend; alternatively, monomer(s) and coordinator can be added to the initiator. Both randomization and vinyl content (i.e., 1,2-microstructure) can be increased through inclusion of a coordinator, usually a polar compound. Up to 90 or more equivalents of coordinator can be used per equivalent of initiator, with the amount depending on, for example, the amount of vinyl content desired, the level of non-polyene monomer employed, the reaction temperature, and nature of the specific coordinator employed. Compounds useful as coordinators include organic compounds that include a heteroatom having a non-bonded pair of electrons (e.g., O or N). Examples include dialkyl ethers of mono- and oligo-alkylene glycols; crown ethers; tertiary amines such as tetramethylethylene diamine; THF; THF oligomers; linear and cyclic oligomeric oxolanyl alkanes (see, e.g., U.S. Pat. No. 4,429,091) such as 2,2'-di(tetrahydrofuryl) propane, di-piperidyl ethane, hexamethylphosphoramide, N,N'-dimethylpiperazine, diazabicyclooctane, diethyl ether, tributylamine, and the like.

Typically, a solution of polymerization solvent(s) and the monomer(s) is provided at a temperature of from about −80° to +100° C., more commonly from about −40° to +50° C., and typically from ~0° to +30° C.; to this solution is added an initiating compound or, where a functionalizing unit is to be provided from the initiator, and the $R^1$-containing initiator (or its precursor with an organolithium, typically an alkyllithium). The solution can have a temperature of from about −70° to ~150° C., more commonly from about −20° to ~120° C., and typically from ~10° to ~100° C. The polymerization is allowed to proceed under anhydrous, anaerobic conditions for a period of time sufficient to result in the formation of the desired polymer, usually from ~0.01 to ~100 hours, more commonly from ~0.08 to ~48 hours, and typically from ~0.15 to ~2 hours. After a desired degree of conversion has been reached, the heat source (if used) can be removed and, if the reaction vessel is to be reserved solely for polymerizations, the reaction mixture is removed to a post-polymerization vessel for functionalization and/or quenching.

Polymers made according to anionic techniques generally have a number average molecular weight ($M_n$) of up to 500,000 Daltons. In certain embodiments, the $M_n$ can be as low as ~2000 Daltons; in these and/or other embodiments, the $M_n$ advantageously can be at least ~10,000 Daltons or can range from ~50,000 to ~250,000 Daltons or from ~75,000 to ~150,000 Daltons. Often, the $M_n$ is such that a quenched sample exhibits a gum Mooney viscosity ($ML_4$/100° C.) of from ~2 to ~150, more commonly from ~2.5 to ~125, even more commonly from ~5 to ~100, and most commonly from ~10 to ~75.

Certain end use applications call for polymers that have properties that can be difficult or inefficient to achieve via anionic (living) polymerizations. For example, in some applications, conjugated diene polymers having high cis-1,4-linkage contents can be desirable. Polydienes can be prepared by processes using catalysts (as opposed to the initiators employed in living polymerizations) and may display pseudo-living characteristics.

Certain types of catalyst systems are known to be useful in producing very stereospecific 1,4-polydienes from conjugated diene monomers. Some catalyst systems preferentially result in cis-1,4-polydienes, while others preferentially provide trans-1,4-polydienes, and the ordinarily skilled artisan is familiar with examples of each type. The following description is based on a particular cis-specific catalyst system, although this merely is for sake of exemplification and is not considered to be limiting to the functionalizing method and compounds.

Exemplary catalyst systems can employ lanthanide metals which are known to be useful for polymerizing conjugated diene monomers. Specifically, catalyst systems that include a lanthanide compound can be used to provide cis-1,4-polydienes from one or more types of conjugated dienes. Preferred lanthanide-based catalyst compositions include those described in U.S. Pat. No. 6,699,813 and patent documents cited therein. A condensed description is provided here for convenience and ease of reference.

Exemplary lanthanide catalyst compositions include (a) a lanthanide compound, an alkylating agent and a halogen-containing compound (although use of a halogen-containing compound is optional when the lanthanide compound and/or the alkylating agent contains a halogen atom); (b) a lanthanide compound and an aluminoxane; or (c) a lanthanide compound, an alkylating agent, and a non-coordinating anion or precursor thereof.

Various lanthanide compounds or mixtures thereof can be employed, with preference given to those which are soluble in aromatic, aliphatic, and/or cycloaliphatic liquids, although hydrocarbon-insoluble lanthanide compounds can be suspended in the polymerization medium. Preferred lanthanide compounds include those which include at least one Nd, La, or Sm atom or those including didymium. The lanthanide atom(s) in the lanthanide compounds can be in any of a number of oxidation states, although the +3 oxidation state is most common. Exemplary lanthanide compounds include carboxylates, organophosphates, organophosphonates, organophosphinates, xanthates, carbamates, dithiocarbamates, β-diketonates, alkoxides, aryloxides, halides, pseudo-halides, oxyhalides, etc.

Typically, the lanthanide compound is used in conjunction with one or more alkylating agents, i.e., organometallic compounds that can transfer hydrocarbyl groups to another metal. These agents typically are organometallic compounds of electropositive metals such as Groups 1, 2, and 3 metals. Exemplary alkylating agents include organoaluminum compounds and organomagnesium compounds. The former include (1) compounds having the general formula $AlR^9_n X_{3-n}'$ where n is an integer of from 1 to 3 inclusive, each $R^9$ independently is a monovalent organic group (which may contain heteroatoms such as N, O, B, Si, S, P, and the like) connected to the Al atom via a C atom and each X' independently is a hydrogen atom, a halogen atom, a carboxylate group, an alkoxide group, or an aryloxide group; and (2) oligomeric linear or cyclic aluminoxanes, which can be made by reacting trihydrocarbylaluminum compounds with water. The latter include compounds having the general formula $MgR^{10}_y X_{2-y}'$ where X' is defined as above, y is an integer of from 1 to 2 inclusive, and $R^{10}$ is the same as $R^9$ except that each monovalent organic group is connected to the Mg atom via a C atom.

Some catalyst compositions contain compounds with one or more labile halogen atoms. Useful halogen-containing compounds include elemental halogens, mixed halogens, hydrogen halides, organic halides, inorganic halides, metallic halides, organometallic halides, and mixtures thereof. The halogen-containing compounds preferably are soluble in solvents such as those described above with respect to lanthanide compounds, although hydrocarbon-insoluble compounds can be suspended in the polymerization medium.

Other catalyst compositions contain a non-coordinating anion or a non-coordinating anion precursor. Exemplary non-coordinating anions include tetraarylborate anions, particularly fluorinated tetraarylborate anions, and ionic compounds containing non-coordinating anions and a countercation (e.g., triphenylcarbonium tetrakis(pentafluorophenyl) borate). Exemplary non-coordinating anion precursors include boron compounds that include strong electron-withdrawing groups.

Catalyst compositions of this type have very high catalytic activity for polymerizing conjugated dienes into stereospecific polydienes over a wide range of concentrations and ratios, although polymers having the most desirable properties typically are obtained from systems that employ a relatively narrow range of concentrations and ratios of ingredients. Further, the catalyst ingredients are believed to interact to form an active catalyst species, so the optimum concentration for any one ingredient can depend on the concentrations of the other ingredients. The following molar ratios are considered to be relatively exemplary for a variety of different systems based on the foregoing ingredients:

alkylating agent to lanthanide compound (alkylating agent/Ln): from ~1:1 to ~200:1, preferably from ~2:1 to ~100:1, more preferably from ~5:1 to ~50:1;

halogen-containing compound to lanthanide compound (halogen atom/Ln): from ~1:2 to ~20:1, preferably from ~1:1 to ~10:1, more preferably from ~2:1 to ~6:1;

aluminoxane to lanthanide compound, specifically equivalents of aluminum atoms on the aluminoxane to equivalents of lanthanide atoms in the lanthanide compound (Al/Ln): from ~10:1 to ~50,000:1, preferably from ~75:1 to ~30,000:1, more preferably from ~100:1 to ~1,000:1; and non-coordinating anion or precursor to lanthanide compound (An/Ln): from ~1:2 to ~20:1, preferably from ~3:4 to ~10:1, more preferably from ~1:1 to ~6:1.

The molecular weight of polydienes produced with lanthanide-based catalysts can be controlled by adjusting the amount of catalyst and/or the amounts of co-catalyst concentrations within the catalyst system. In general, increasing the catalyst and co-catalyst concentrations reduces the molecular weight of resulting polydienes, although very low molecular weight polydienes (e.g., liquid polydienes) require extremely high catalyst concentrations which necessitates removal of catalyst residues from the polymer to avoid adverse effects such as retardation of the sulfur cure rate. Including one or more Ni-containing compounds to lanthanide-based catalyst compositions advantageously permits easy regulation of the molecular weight of the resulting polydiene without significant negative effects on catalyst activity and polymer microstructure. Various Ni-containing compounds or mixtures thereof can be employed, with preference given to those which are soluble in hydrocarbon solvents such as those set forth above.

The Ni atom in the Ni-containing compounds can be in any of a number of oxidation states, although divalent Ni compounds, where the Ni atom is in the +2 oxidation state, generally are preferred. Exemplary Ni compounds include carboxylates, organophosphates, organophosphonates, organophosphinates, xanthates, carbamates, dithiocarbamates, β-diketonates, alkoxides, aryloxides, halides, pseudohalides, oxyhalides, organonickel compounds (i.e., compounds containing at least one C—Ni bond such as, for example, nickelocene, decamethyl-nickelocene, etc.), and the like.

The molar ratio of the Ni-containing compound to the lanthanide compound (Ni/Ln) generally ranges from ~1:1000 to ~1:1, preferably from ~1:200 to ~1:2, and more preferably from ~1:100 to ~1:5.

These types of catalyst compositions can be formed using any of the following methods:

(1) In situ. The catalyst ingredients are added to a solution containing monomer and solvent (or simply bulk monomer). The addition can occur in a stepwise or simultaneous manner. In the case of the latter, the alkylating agent preferably is added first followed by, in order, the lanthanide compound, the nickel-containing compound (if used), and (if used) the halogen-containing compound or the non-coordinating anion or non-coordinating anion precursor.

(2) Pre-mixed. The ingredients can be mixed outside the polymerization system, generally at a temperature of from about −20° to about 80° C., before being introduced to the conjugated diene monomer(s).

(3) Pre-formed in the presence of monomer(s). The catalyst ingredients are mixed in the presence of a small amount of conjugated diene monomer(s) at a temperature of from about −20° to ~80° C. The amount of conjugated diene monomer can range from ~1 to ~500 moles, preferably from ~5 to ~250 moles, and more preferably from ~10 to ~100 moles, per mole of the lanthanide compound. The resulting catalyst composition is added to the remainder of the conjugated diene monomer(s) to be polymerized.

(4) Two-stage procedure.
(a) The alkylating agent is combined with the lanthanide compound in the absence of conjugated diene monomer, or in the presence of a small amount of conjugated diene monomer, at a temperature of from about −20° to ~80° C.
(b) The foregoing mixture and the remaining components are charged in either a stepwise or simultaneous manner to the remainder of the conjugated diene monomer(s) to be polymerized.
(The Ni-containing compound, if used, can be included in either stage.)

When a solution of one or more of the catalyst ingredients is prepared outside the polymerization system in the foregoing methods, an organic solvent or carrier is preferably employed. Useful organic solvents include those mentioned previously.

The production of cis-1,4-polydiene is accomplished by polymerizing conjugated diene monomer in the presence of a catalytically effective amount of a catalyst composition. The total catalyst concentration to be employed in the polymerization mass depends on the interplay of various factors such as the purity of the ingredients, the polymerization temperature, the polymerization rate and conversion desired, the molecular weight desired, and many other factors; accordingly, a specific total catalyst concentration cannot be definitively set forth except to say that catalytically effective amounts of the respective catalyst ingredients should be used. The amount of the lanthanide compound used generally ranges from ~0.01 to ~2 mmol, preferably from ~0.02 to ~1 mmol, and more preferably from ~0.03 to ~0.5 mmol per 100 g conjugated diene monomer. All other ingredients generally are added in amounts that are based on the amount of lanthanide compound (see the various ratios set forth previously).

Polymerization preferably is carried out in an organic solvent, i.e., as a solution or precipitation polymerization where the monomer is in a condensed phase. The catalyst ingredients preferably are solubilized or suspended within the organic liquid. The amount (wt. %) of monomer present in the polymerization medium at the beginning of the polymerization generally ranges from ~3 to ~80%, preferably ~5 to ~50%, and more preferably ~10% to ~30%. (Polymerization also can be carried out by means of bulk polymerization conducted either in a condensed liquid phase or in a gas phase.)

Regardless of whether a batch, continuous, or semi-continuous process is employed, the polymerization preferably is conducted with moderate to vigorous agitation under anaerobic conditions provided by an inert protective gas. The polymerization temperature may vary widely, although typically a temperature of from ~20° to ~90° C. is employed; heat can be removed by external cooling and/or cooling by evaporation of the monomer or the solvent. The polymerization pressure employed may vary widely, although typically a pressure of from about 0.1 to about 1 MPa is employed.

Where 1,3-butadiene is polymerized, the cis-1,4-polybutadiene generally has a $M_n$, as determined by GPC using polystyrene standards, of from ~5000 to ~200,000 Daltons, from ~25,000 to ~150,000 Daltons, or from ~50,000 to ~125,000 Daltons. The polydispersity of the polymers generally ranges from ~1.5 to ~5.0, typically from ~2.0 to ~4.0.

Resulting polydienes advantageously can have a cis-1,4-linkage content of at least ~60%, at least ~75%, at least ~90%, and even at least ~95%, and a 1,2-linkage content of less than ~7%, less than ~5%, less than ~2%, and even less than ~1%.

Regardless of the type of polymerization process employed, at this point the reaction mixture commonly is referred to as a "polymer cement" because of its relatively high concentration of polymer.

Providing a terminal functionality of the type set forth above in formula (IV) can be achieved by functionalizing the polymer prior to quenching, advantageously when it is in the above-described polymer cement state. One method of effecting this functionalization involves introducing to the polymer cement one or more aromatic compounds that include a group capable of reacting with terminally active polymers as well as one or more hydroxyl groups or hydrolyzable groups (i.e., one or more $OR^4$ substituents) and allowing such compound(s) to react at a terminus of a reactive polymer chain. This type of compound hereinafter is referred to as a terminating compound.

Where the terminating compound includes more than one $OR^4$ substituent, each can be on the same ring of the aryl group, or two or more can be on different rings within the aryl group. Where the aryl group contains three or more $OR^4$ substituents, all of them can be on the same ring, two of them can be on one ring with the other(s) being on other ring(s), or each of them can be on separate rings.

A preferred group of terminating compounds include those with an aryl group having at least two $OR^4$ substituents and, among these, preferred are those where at least two of the $OR^4$ substituents are on the same ring of the aryl group. Among the latter, particularly preferred are those with $OR^4$ substituents at the 3 and 4 positions of the same ring within the aryl group, preferably a phenyl group.

Examples of compounds that can be used to provide functionality such as that shown in formula (IV) include those with the following general formulas:

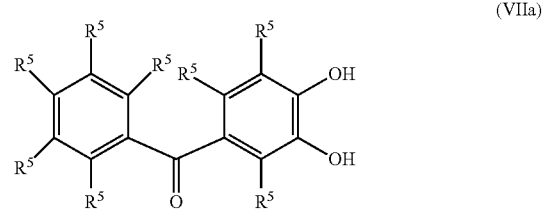

(VIIa)

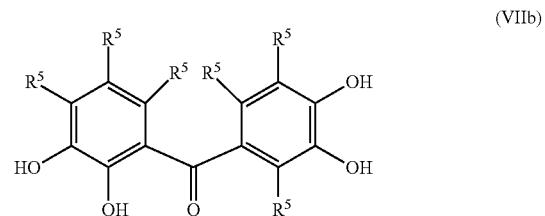

(VIIb)

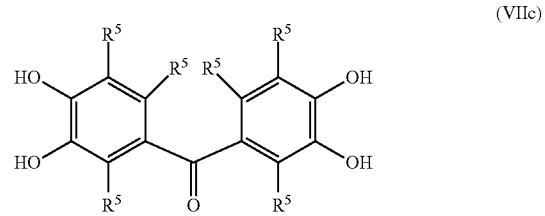

(VIIc)

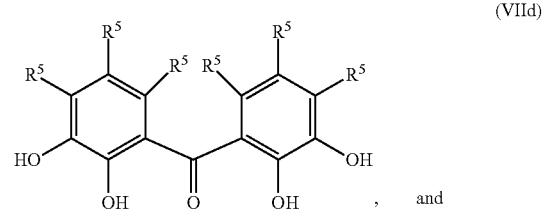

(VIId)

, and

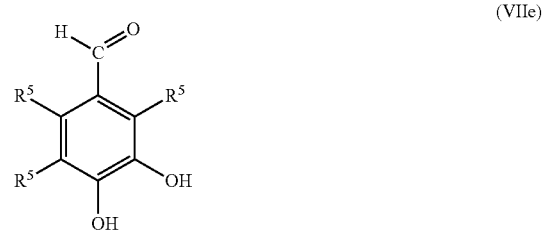

(VIIe)

where each $R^5$ independently is a hydrogen atom, a hydroxyl group, an alkoxy group, or a hydrocarbyl group, preferably an alkyl group and more preferably a $C_1$-$C_3$ alkyl group; in certain embodiments, each $R^5$ can be H. In addition to the foregoing, two or more $R^5$ groups together can form another ring such as, for example, anthrones and flavones:

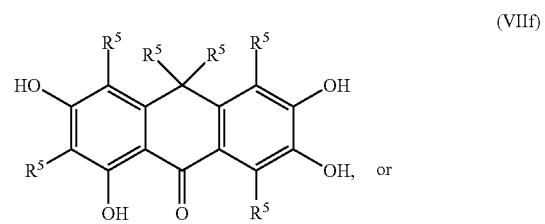

(VIIf)

, or

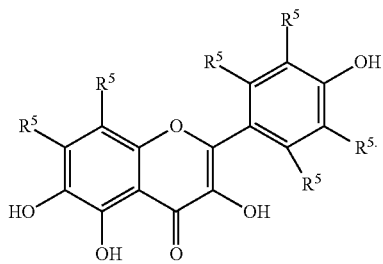
(VIIg)

By comparing formulas (VIIf) and (VIIg) to formula (IV) above, one can see that, in the terminal functionality represented by formula (IV), $R^6$ and a portion of $R^3$ can be linked so that, together with the atom(s) to which each is attached (directly or indirectly), they form a ring that is bound to or fused with the $R^3$ aryl group; this can be represented pictorially by the general formula

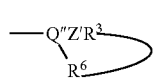
(IVb)

where each of the variables is defined as before.

The foregoing are to be considered exemplary and not limiting. For example, each of the foregoing representative compounds include adjacent hydroxyl substituent groups (although formula (VIIf) does include one ring with non-adjacent hydroxyl substituents) but, as already described, the hydroxyl substituents need not be adjacent. Not specifically shown in the foregoing formulas (VIIa)-(VIIg) but included within the scope of useful compounds are those having aryl groups other than phenyl groups, those having aryl groups not directly bonded to the carbonyl C atom, those with the carbonyl C atom bonded to an S atom rather than O (i.e., thioketo analogs), those where Z' is other than a single bond, and the like. Where $R^3$ is other than a phenyl group, the hydroxyl substituent groups can be on the same or different rings; when they are on more than one ring, it is preferred that they be at least somewhat proximate, i.e., that they be directly bonded to ring C atoms that are separated by no more than 4, preferably 3, and even more preferably 2, other ring atoms.

Further, as suggested above, the compound itself need not include hydroxyl groups and, instead, can include groups that are easily hydrolyzable so as to provide hydroxyl groups after reaction. Protected compounds generally have structures similar to those set forth above with respect to formulas (VIIa)-(VIIg) with OR groups in place of some or all of the OH groups. By way of non-limiting example, a protected compound generally analogous to the compound from formula (VIIa), with each $R^5$ being H, can be represented by

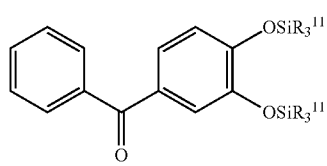
(VIII)

where each $R^{11}$ independently is a hydrocarbyl group, e.g., a linear or branched alkyl group. Variations similar to those described above with respect to the hydroxyl-containing compounds are envisioned for the protected compounds.

Each of the compounds represented by formulas (VIIa)-(VIIg) and (VIII) include a carbonyl group. Carbonyl groups provide convenient points for reaction with and attachment to carbanionic polymer chains. Non-limiting examples of other potentially useful reactive groups include aldehyde, (thio)ketone, (thio)ester, di(thio)ester, amide, epoxy, halosilane, and the like.

Reaction of these types of compound with a pre-made reactive polymer can be performed relatively quickly (a few minutes to a few hours) at moderate temperatures (e.g., 0° to 75° C.).

The amount of such compounds to be reacted with pre-made reactive polymers can vary widely, depending significantly on the degree of desired effect, the amount of non-conventional filler(s) employed, the ratio of conventional-to-non-conventional filler particles, and the like. Based on the amount of reactive polymer chains (generally determined based on the equivalents of initiator or catalyst), the amount of compounds generally corresponding to formulas (VIIa)-(VIIg) and (VIII) can range from about 1:10 to about 5:4, generally from about 1:5 to about 9:8, and typically from about 1:2 to about 1:1.

Lesser amounts of terminating compounds of the type just described can be employed in certain embodiments so as to preserve some reactive polymer terminals for reaction with other functionalizing agents, which can be added before, after, or with the compounds just discussed; this type of multiple functionalization can be avoided, at least to some extent, through use of functional initiators as discussed previously. Also, at least some embodiments of polymers having functionalities defined by formulas (IV) and (IVb), as well as protected analogs, can exhibit excellent interactivity with carbon black and silica, thereby avoiding the need for multiple functionalization reactions.

Where the foregoing type of terminating compound is not employed but the macromolecule includes at least one functionalizing unit derived from either or both of the initiator and a formula (V)-type monomer, additional functionalization can result from termination with a heteroatom-containing compound including, but not limited to, Sn, Si, and N. Specific examples of alternative or additional terminating compounds include 1,3-dimethyl-2-imidazolidinone (DMI), 3-bis(trimethylsilyl)aminopropyl-methyldiethoxysilane (APMDEOS), as well as those described in U.S. Pat. Nos. 3,109,871, 4,647,625, 4,677,153, 5,109,907, and 6,977,281, and references cited in, and later publications citing, these patents. This type of functionalization is described below in Examples 73-75.

At this point, the resulting polymer includes one or more types of polyene mer and at least one functionalizing unit which includes an aryl group having at least one directly bonded $OR^4$ substituent. The functionalizing unit(s) can be derived from the initiating compound, the monomer(s), or a terminating compound. In certain aspects, more than one of the functionalizing units can be incorporated, and these can result from multiple mer, from an initiator plus one or more mer, a terminating group plus one or more mer, or from all three.

The identity of the $R^4$ moiety of the substituent (i.e., whether it is a H atom or a protecting group) depends on the origin of the unit of which it is a part. Units derived from an initiator and/or monomers will have OR groups while units derived from a terminating compound can have OR or OH groups. Ensuring that most, preferably all, R moieties are converted to H atoms typically is desirable so as to promote maximum interactivity with filler particles (when the polymer is used as part of a rubber composition). The processing steps (including quenching) described below can be sufficient to hydrolyze at least some of the R moieties, thereby providing one or more hydroxyl substituents to one or more aryl groups within polymer. Alternatively, a separate reaction step designed to promote extensive, preferably complete, hydrolysis can be employed; from the exemplary technique employed in several of the examples below, the ordinarily skilled artisan can envision other potentially effective reactions. Further, the ordinarily skilled artisan understands that OR or OH groups, whether present in an $R^1$ group, $R^3$ group, $R^6$ group, or elsewhere, may undergo further reaction during this processing and/or compounding with one or more types of particulate fillers (described below).

Quenching can be conducted by stirring the polymer and an active hydrogen-containing compound, such as an alcohol or acid, for up to about 120 minutes at temperatures of from about 25° to about 150° C.

Solvent can be removed from the quenched polymer cement by conventional techniques such as drum drying, extruder drying, vacuum drying or the like, which may be combined with coagulation with water, alcohol or steam, thermal desolvation, etc.; if coagulation is performed, oven drying may be desirable.

The resulting polymer can be utilized in a tread stock compound or can be blended with any conventionally employed tread stock rubber including natural rubber and/or non-functionalized synthetic rubbers such as, e.g., one or more of homo- and interpolymers that include just polyene-derived mer units (e.g., poly(butadiene), poly(isoprene), and copolymers incorporating butadiene, isoprene, and the like), SBR, butyl rubber, neoprene, EPR, EPDM, NBR, silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from about 5 to about 99% of the total rubber, with the conventional rubber(s) making up the balance of the total rubber. The minimum amount depends to a significant extent on the degree of hysteresis reduction desired.

Elastomeric compounds typically are filled to a volume fraction, which is the total volume of filler(s) added divided by the total volume of the elastomeric stock, of about 25%; accordingly, typical (combined) amounts of reinforcing fillers is about 30 to 100 phr.

Potentially useful carbon black materials include, but not limited to, furnace blacks, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semi-reinforcing furnace blacks, medium processing channel blacks, hard processing channel blacks, conducting channel blacks, and acetylene blacks; mixtures of two or more of these can be used. Carbon blacks having a surface area (EMSA) of at least 20 m$^2$/g, preferably at least about 35 m$^2$/g, are preferred; surface area values can be determined by ASTM D-1765. The carbon blacks may be in pelletized form or an unpelletized flocculent mass, although unpelletized carbon black can be preferred for use in certain mixers.

The amount of carbon black utilized historically has been up to ~50 parts by weight (pbw) per 100 parts of polymer (phr), with ~5 to ~40 phr being typical. For certain oil-extended formulations, the amount of carbon black has been even higher, e.g., on the order of ~80 phr.

Amorphous silica ($SiO_2$) also commonly is used as a filler. Silicas typically are produced by a chemical reaction in water, from which they are precipitated as ultrafine, spherical particles which strongly associate into aggregates and, in turn, combine less strongly into agglomerates. Surface area gives a reliable measure of the reinforcing character of different silicas, with BET (see; Brunauer et al., *J. Am. Chem. Soc.*, vol. 60, p. 309 et seq.) surface areas of less than 450 m$^2$/g, commonly between ~32 to ~400 m$^2$/g, and typically ~100 to ~250 m$^2$/g, generally being considered useful. Commercial suppliers of silica include PPG Industries, Inc. (Pittsburgh, Pa.), Grace Davison (Baltimore, Md.), Degussa Corp. (Parsippany, N.J.), Rhodia Silica Systems (Cranbury, N.J.), and J.M. Huber Corp. (Edison, N.J.).

When silica is employed as a reinforcing filler, addition of a coupling agent such as a silane is customary so as to ensure good mixing in, and interaction with, the elastomer(s). Generally, the amount of silane that is added ranges between about 4 and 20%, based on the weight of silica filler present in the compound. Coupling agents can have a general formula of A-T-G, in which A represents a functional group capable of bonding physically and/or chemically with a group on the surface of the silica filler (e.g., surface silanol groups); T represents a hydrocarbon group linkage; and G represents a functional group capable of bonding with the elastomer (e.g., via a sulfur-containing linkage). Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes bearing the G and A functionalities mentioned above. Addition of a processing aid can be used to reduce the amount of silane employed; see, e.g., U.S. Pat. No. 6,525,118 for a description of fatty acid esters of sugars used as processing aids. Additional fillers useful as processing aids include mineral fillers, such as clay (hydrous aluminum silicate), talc (hydrous magnesium silicate), and mica as well as non-mineral fillers such as urea and sodium sulfate. Preferred micas contain principally alumina, silica and potash, although other variants also can be useful. The additional fillers can be utilized in an amount of up to about 40 phr, typically up to about 20 phr.

Silica commonly is employed in amounts of up to ~100 phr, typically from ~5 to ~80 phr. The useful upper range is limited by the high viscosity that such fillers can impart. When carbon black also is used, the amount of silica can be decreased to as low as ~1 phr; as the amount of silica decreases, lesser amounts of the processing aids, plus silane if any, can be employed.

One or more non-conventional fillers having relatively high interfacial free energies, i.e., surface free energy in water values ($\gamma_{pl}$) preferably are used in conjunction with or in place of carbon black and/or silica. The term "relatively high" can be defined or characterized in a variety of ways such as, e.g., greater than that of the water-air interface, preferably several multiples (e.g., at least 2×, at least 3× or even at least 4×) of this value; at least several multiples (e.g., at least 2×, at least 3×, at least 4×, at least 5×, at least 6×, at least 7×, at least 8×, at least 9× or even at least 10×) of the $\gamma_{pl}$ value for amorphous silica; in absolute terms such as, e.g., at least ~300, at least ~400, at least ~500, at least ~600, at least ~700, at least ~750, at least ~1000, at least ~1500, and at least ~2000 mJ/m$^2$; in ranges such as, e.g., from ~300 to ~5000 mJ/m$^2$, from ~350 to ~4000 mJ/m$^2$, from ~400 to ~5000 mJ/m$^2$, from ~450 to ~4000 mJ/m$^2$, from ~500 to ~5000 mJ/m$^2$, and various sub-ranges within the foregoing and/or other combinations of high and low values; and the like.

Non-limiting examples of naturally occurring materials with relatively high interfacial free energies include F-apatite, goethite, hematite, zincite, tenorite, gibbsite, quartz, kaolinite, all forms of pyrite, and the like. Certain synthetic complex oxides also can exhibit this type of high interfacial free energy.

The foregoing types of materials typically are more dense than either carbon black or amorphous silica; thus, replacing a particular mass of carbon black or silica with an equal mass of a non-conventional filler typically will result in a much smaller volume of overall filler being present in a given compound. Accordingly, replacement typically is made on an equal volume, as opposed to equal weight, basis.

Generally, ~5 to ~60% of the conventional particulate filler material(s) can be replaced with an approximately equivalent (~0.8× to ~1.2×) volume of non-conventional filler particles. In certain embodiments, replacing ~10 to ~58% of the conventional particulate filler material(s) with an approximately equivalent (~0.85× to ~1.15×) volume of other filler particles is sufficient; in other embodiments, replacing ~15 to ~55% of the conventional particulate filler material(s) with an approximately equivalent (~0.9× to ~1.1×) volume of other filler particles is adequate; in still other embodiments, replacing ~18 to ~53% of the conventional particulate filler material(s) with an approximately equivalent (~0.95× to ~1.05×) volume of other filler particles can be preferable.

The weight inequality issue might be able to be overcome or ameliorated by employing non-standard particles. For example, one can envision essentially hollow particles of one or more types of non-conventional fillers as well as relatively light particles coated so as to have a surface that includes one or more of types of non-conventional filler compounds.

The non-conventional filler particles generally can be of approximately the same size as the conventional fillers employed in compounds. In other words, neither extremely large particles such as those employed in the aforementioned U.S. Pat. No. 5,066,702 nor extremely small particles such as those employed in the aforementioned U.S. Pat. No. 6,972,307 are required. In general, relatively small particles are preferred both for reinforcement purposes and to ensure a large number of particles are available at the tread surface.

Other conventional rubber additives also can be added. These include, for example, process oils, plasticizers, anti-degradants such as antioxidants and antiozonants, curing agents and the like.

All ingredients can be mixed with standard equipment such as, e.g., Banbury or Brabender mixers. Typically, mixing occurs in two or more stages. During the first stage (also known as the masterbatch stage), mixing typically is begun at temperatures of ~120° to ~130° C. and increases until a so-called drop temperature, typically ~165° C., is reached.

Where a formulation includes fillers other than carbon black, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with about 0.2 to about 5 phr of one or more known vulcanizing agents such as, for example, sulfur or peroxide-based curing systems. For a general disclosure of suitable vulcanizing agents, the interested reader is directed to an overview such as that provided in Kirk-Othmer, Encyclopedia of Chem. Tech., 3d ed., (Wiley Interscience, New York, 1982), vol. 20, pp. 365-468. Vulcanizing agents, accelerators, etc., are added at a final mixing stage. To avoid undesirable scorching and/or premature onset of vulcanization, this mixing step often is done at lower temperatures, e.g., starting at ~60° to ~65° C. and not going higher than ~105° to ~110° C.

Subsequently, the compounded mixture is processed (e.g., milled) into sheets prior to being formed into any of a variety of components and then vulcanized, which typically occurs at ~5° to ~15° C. higher than the highest temperatures employed during the mixing stages, most commonly about 170° C.

The following non-limiting, illustrative examples provide detailed conditions and materials that can be useful in the practice of the invention just described.

EXAMPLES

In all examples, dried glass vessels previously sealed with extracted septum liners and perforated crown caps under a positive $N_2$ purge were used for all preparations.

All nuclear magnetic resonance (NMR) testing was performed on a Varian™ 300 MHz spectrometer (Varian, Inc.; Palo Alto, Calif.).

Data corresponding to "Bound rubber" were determined using the procedure described by J. J. Brennan et al., *Rubber Chem. and Tech.*, 40, 817 (1967).

Cold flow testing was performed using a Scott™ tester. Samples were prepared by melt pressing 2.5 g of polymer at 100° C. for 20 minutes in a mold using a preheated press. The resulting cylindrical samples, which had a uniform thickness of ~12 mm, were allowed to cool to room temperature before being removed from the mold. Samples were placed individually under the weight of a 5 kg calibrated weight. Tests were conducted for ~30 min. for SBR samples and ~8 min. for polybutadiene samples (measured from time that the weight was released), with sample thicknesses being recorded as a function of time. Sample thickness at the conclusion of the appropriate time (~30 min. or ~8 min.) generally is considered to be an acceptable indicator of cold flow resistance.

Mooney viscosity ($ML_{1+4}$) values were determined with an Alpha Technologies™ Mooney viscometer (large rotor) using a one-minute warm-up time and a four-minute running time; tensile mechanical properties were determined using the standard procedure described in ASTM-D412; Payne effect ($\Delta G'$, i.e., the difference between G' at 0.25% strain and at 14% strain) and hysteresis (tan δ) data were obtained from dynamic experiments conducted at 60° C. and 10 Hz (strain sweep) and 2% strain and 10 Hz (temperature sweep). With respect to tensile properties, $M_Y$ is modulus at Y % elongation, $T_b$ is tensile strength at break, and $E_b$ is percent elongation at break.

A. Examples 1-33 (Terminators)

In these examples, styrene (33% in hexane), hexane, n-butyllithium (1.60 M in hexane), 2,2-bis(2'-tetrahydrofuryl)propane (1.6 M solution in hexane, stored over CaH$_2$), and 2,6-di-tert-butyl-4-methylphenol (BHT) solution in hexane were used.

Commercially available reagents and starting materials included the following, all of which were acquired from Sigma-Aldrich Co. (St. Louis, Mo.) and used without further purification unless otherwise noted in a specific example: 3,4-dihydroxybenzaldehyde, 3,4-dihydroxybenzophenone, imidazole, t-butyl(chloro)dimethylsilane, diethyl ether, NH$_4$Cl, MgSO$_4$ (anhydrous), THF, ethyl acetate, methylaluminoxane (MAO), diisobutylaluminum hydride, HMI, diethylaluminum chloride, 4,4'-bis(diethylamino)benzophenone (DEAB), and tetrabutyl-ammonium fluoride (TBAF).

Testing data in most of the Examples was performed on filled compositions made according to the formulations shown below in Table 1a (titanium oxide, rutile), Table 1b (carbon black and aluminum hydroxide), Table 1c (carbon black and titanium oxide), and Table 1d (carbon black).

The titania employed in these formulations was Tronox™ CR-834 alumina-stabilized TiO$_2$ with a particle size of ~0.17 μm and a specific gravity of ~4.2 (Tronox Inc.; Oklahoma City, Okla.), and the aluminum hydroxide employed was Hydral™ PGA-HD Al(OH)$_3$ particles with a median particle diameter of ~1 μm and a density of 2.42 g/cm$^3$ (Almatis, Inc.; Leetsdale, Pa.). In these (and similar subsequent tables), N-phenyl-N'-(1,3-dimethylbutyl)-p-phenylenediamine (6PPD) acts as an antioxidant, and 2,2'-dithiobis (benzothiazole) (MBTS), N-tert-butylbenzothiazole-2-sulfenamide (TBBS) and N,N'-diphenylguanidine (DPG) act as accelerators. Black oil is an extender oil that contains a relatively low amount of polycyclic aromatic (PCA) compounds.

TABLE 1a

Compound formulation, titania

| | Amount (phr) |
|---|---|
| Masterbatch | |
| synthetic polymer | 100 |
| TiO$_2$ | 116.7 |
| 6PPD | 1 |
| stearic acid | 2 |
| Final | |
| sulfur | 1.3 |
| ZnO | 3 |
| TBBS | 1 |
| MBTS | 1 |
| DPG | 0.5 |
| TOTAL | 226.5 |

TABLE 1b

Compound formulation, carbon black and aluminum hydroxide

| | Amount (phr) |
|---|---|
| Masterbatch | |
| synthetic polymer | 100 |
| carbon black (N339 type) | 25 |
| Al(OH)$_3$ | 33.6 |
| 6PPD | 1 |
| stearic acid | 2 |
| Final | |
| sulfur | 1.5 |
| ZnO | 3 |
| MBTS | 1 |
| DPG | 0.5 |
| TOTAL | 167.6 |

TABLE 1c

Compound formulation, carbon black and titania

| | Amount (phr) |
|---|---|
| Masterbatch | |
| synthetic polymer | 100 |
| carbon black (N339 type) | 25 |
| TiO$_2$ | 58.3 |
| 6PPD | 1 |
| stearic acid | 2 |
| Final | |
| sulfur | 1.3 |
| ZnO | 3 |
| TBBS | 1 |
| MBTS | 1 |
| DPG | 0.5 |
| TOTAL | 193.1 |

TABLE 1d

Compound formulation, carbon black

| | Amount (phr) |
|---|---|
| Masterbatch | |
| synthetic polymer | 80 |
| polyisoprene | 20 |
| carbon black (N343 type) | 50 |
| wax | 2 |
| 6PPD | 1 |
| stearic acid | 2 |
| black oil | 10 |
| Final | |
| sulfur | 1.5 |
| ZnO | 2.5 |
| MBTS | 0.5 |
| TBBS | 0.5 |
| DPG | 0.3 |
| TOTAL | 170.3 |

Example 1: Synthesis of 3,4-bis(tert-butyldimethylsilyloxy)benzophenone

To a dry flask under nitrogen was charged ~6.0 g 3,4-dihydroxybenzophenone, ~6.3 g triethylamine, ~0.14 g 4-(dimethylamino)pyridine, and 30 mL DMF. A solution of ~9.3 g tert-butyl(chloro)dimethylsilane in 30 mL DMF then was added in dropwise fashion.

The reaction mixture was stirred for ~4 hours at room temperature before being poured into ~100 mL hexane and ~30 mL saturated NH$_4$Cl solution. The organic phase was washed three times with 50 mL portions of water and dried with anhydrous MgSO$_4$.

After solvent was removed, the residue was separated by a flash silica-gel column with hexane/ethyl acetate (85:15, v/v) as eluent. Approximately 11.5 g (93% yield) white solid was obtained. Proton and $^{13}$C NMR spectroscopic analysis confirmed the product as 3,4-bis(tert-butyldimethylsilyloxy) benzophenone (BTBDMSBP).

Example 2: Synthesis of 3,4-bis(tert-butyldimethylsilyloxy)benzaldehyde

To a dry flask under nitrogen was charged ~10.0 g 3,4-dihydroxybenzaldehyde, ~16.1 g triethylamine, ~0.35 g 4-(dimethylamino)pyridine, and 60 mL DMF. A solution of ~24.0 g tert-butyl(chloro)dimethylsilane in 60 mL DMF then was added in dropwise fashion.

The reaction mixture was stirred for ~4 hours at room temperature before being poured into ~200 mL hexane and ~100 mL saturated NH$_4$Cl solution. The organic phase was washed three times with 100 mL portions of water and dried with anhydrous MgSO$_4$.

After solvent was removed, the residue was separated by a flash silica-gel column with hexane/ethyl acetate (95:5, v/v) as eluent. Approximately 25.5 g (96% yield) white solid was obtained. Proton and $^{13}$C NMR spectroscopic analysis confirmed the product as 3,4-bis(tert-butyldimethylsilyloxy) benzaldehyde (BTBDMSBA).

Examples 3-5: Styrene/Butadiene Copolymers

To a N$_2$-purged reactor equipped with a stirrer was added 1.39 kg hexane, 0.37 kg styrene solution, and 2.27 kg butadiene solution (21.6% by wt. in hexane). The reactor was charged with 3.19 mL n-butyllithium solution, followed by 1.13 mL of 2,2-bis(2'-tetrahydro-furyl)propane solution. The reactor jacket was heated to 50° C., and the polymerization was allowed to continue for ~75 minutes. The polymer cement was cooled to room temperature before being quenched in isopropanol containing 2,6-di-tert-butyl-4-methylphenol and then drum dried. This is designated Example 3 below.

The foregoing polymerization was essentially repeated; however, prior to coagulation, 6.0 mL of a 0.83 M solution of BTBDMSBP (from Example 1) in hexane was added to the reactor, and the polymer cement was agitated for another ~30 minutes at 50° C. before being allowed to cool to room temperature. The polymer cement was transferred to a N$_2$-purged bottle, to which ~130 mL TBAF solution (0.23 M in THF) was added. The bottle was rotated for ~4 hours in a 25° C. water bath followed by another ~30 minutes in a 50° C. water bath. The bottle contents then were coagulated and drum dried as above. This is designated Example 4 below.

The polymerization again was essentially repeated, with the exception that ~2.24 kg of 21.9% by wt. butadiene solution was used. Prior to coagulation, 4.9 mL of a 1.0 M solution of BTBDMSBA (from Example 2) in hexane was added to the reactor, and the polymer cement was processed similarly to the one from Example 4. This is designated as Example 5 below.

The properties of these styrene/butadiene copolymers are summarized in the following table. Molecular weights were determined by GPC using SBR standards, and 1,2-linkage contents were determined from $^1$H NMR spectroscopy.

TABLE 2

Properties of polymers from Examples 3-5

|  | 3 | 4 | 5 |
|---|---|---|---|
| $M_n$ (kg/mol) | 109.5 | 110.0 | 120.3 |
| $M_w/M_n$ | 1.05 | 1.08 | 1.12 |
| $T_g$ (° C.) | −38.4 | −38.4 | −39.2 |
| styrene content (%) | 21.0 | 20.9 | 21.1 |
| 1,2-linkage content (%) | 49.1 | 49.0 | 48.6 |

Examples 6-11: Filled Compositions

The polymers from Examples 3-5 were used with the formulation shown above in Table 1a to provide compositions from which vulcanizates designated as Examples 6-8 below were prepared.

The same polymers were used with the formulation shown above in Table 1b to provide compositions from which vulcanizates designated as Examples 9-11 below were prepared.

Mixing of each compound (i.e., filled composition) was performed with a 65 g Brabender™ internal mixer. After vulcanization under high pressure at high temperature, physical properties of the compounds were determined, and the results are summarized below in Table 3.

TABLE 3

Testing data from Examples 6-11

|  | 6 | 7 | 8 | 9 | 10 | 11 |
|---|---|---|---|---|---|---|
|  | \multicolumn{6}{c}{Compound formulation} |
|  | Table 1a | | | Table 1b | | |
|  | \multicolumn{6}{c}{Polymer used (example no.)} |
|  | 3 | 4 | 5 | 3 | 4 | 5 |
| Shore A hardness @ 23° C. | 40.7 | 48.5 | 48.8 | 57.3 | 58.1 | 57.4 |
| Rebound @ 50° C. | 49.8 | 63.8 | 64.8 | 46.0 | 55.0 | 55.4 |
| Tensile testing, 23° C. | | | | | | |
| Modulus, 50% strain (MPa) | 0.589 | 1.068 | 1.108 | 1.670 | 1.861 | 1.804 |
| Modulus, 100% strain (MPa) | 0.779 | 1.915 | 2.034 | 2.677 | 3.682 | 3.649 |

TABLE 3-continued

Testing data from Examples 6-11

|  | 6 | 7 | 8 | 9 | 10 | 11 |
|---|---|---|---|---|---|---|
|  | Compound formulation | | | | | |
|  | Table 1a | | | Table 1b | | |
|  | Polymer used (example no.) | | | | | |
|  | 3 | 4 | 5 | 3 | 4 | 5 |
| Modulus, 200% strain (MPa) | 1.233 | 4.182 | 4.783 | 5.068 | 7.723 | 8.021 |
| Modulus, 300% strain (MPa) | 1.919 | 5.988 | 7.115 | 8.137 | 12.847 | 13.115 |
| $T_b$ (MPa) | 3.4 | 6.9 | 8.4 | 10.3 | 16.2 | 14.9 |
| $E_b$ (%) | 415.2 | 346.3 | 359.8 | 354.0 | 355.7 | 327.8 |
| Temperature sweep, 10 Hz | | | | | | |
| Temp. at tan δ peak (° C.) | −21.12 | −20.36 | −20.79 | −20.04 | −19.41 | −19.83 |
| G' @ −20° C. and 0.20% strain (MPa) | 50.8 | 23.3 | 20.1 | 104.0 | 59.6 | 49.2 |
| Strain sweep, 60° C. and 10 Hz | | | | | | |
| G' @ 6.96% strain (MPa) | 1.34 | 1.44 | 1.48 | 2.12 | 2.11 | 2.08 |
| tan δ @ 6.96% strain | 0.125 | 0.0585 | 0.0557 | 0.172 | 0.0835 | 0.0799 |

Relative to Examples 6 and 9 (non-functionalized controls), respectively, Examples 7-8 and 10-11 displayed significantly higher room temperature Shore A hardness values, significantly higher rebound values at 50° C. (generally corresponding to reductions in hysteresis), enhanced room temperature tensile strengths, lower modulus values at −20° C. (generally corresponding to better ice traction), higher elastic modulus at 60° C. and high strain (generally corresponding to better handling performance) and significantly lower loss tangent at 60° C. (generally corresponding to reductions in hysteresis).

Examples 12-14: Functionally Initiated Styrene/Butadiene Copolymers

To a $N_2$-purged reactor equipped with a stirrer was added 1.39 kg hexane, 0.37 kg styrene solution, and 2.27 kg butadiene solution (21.6% by wt. in hexane). The reactor was charged with 1.62 mL of 3.0 M HMI in toluene and 3.19 mL n-butyllithium solution, followed by 1.13 mL 2,2-bis (2'-tetrahydrofuryl)propane solution. The reactor jacket was heated to 50° C., and the polymerization was allowed to continue for ~60 minutes. The polymer cement was cooled to room temperature before being quenched and drum dried as described previously. This is designated Example 12 below.

The foregoing polymerization was essentially repeated; however, the polymerization was permitted to continue for ~75 minutes at 50° C. and, prior to coagulation, 6.0 mL of a 0.83 M solution of BTBDMSBP (from Example 1) in hexane was added to the reactor, and the polymer cement was agitated for another ~30 minutes at 50° C. before being allowed to cool to room temperature. The polymer cement was transferred to a $N_2$-purged bottle, to which ~130 mL TBAF solution (0.23 M in THF) was added. The bottle was rotated for ~4 hours in a 25° C. water bath followed by another ~30 minutes in a 50° C. water bath. The bottle contents then were coagulated and drum dried as above. This is designated Example 13 below.

The polymerization and processing described in connection with Example 13 again was essentially repeated, with the exception that ~2.24 kg of 21.9% by wt. butadiene solution was used and, prior to coagulation, 4.9 mL of a 1.0 M solution of BTBDMSBA (from Example 2) in hexane was added to the reactor. This is designated Example 14 below.

The properties of these copolymers are summarized in the following table.

TABLE 4

Properties of polymers from Examples 12-14

|  | 12 | 13 | 14 |
|---|---|---|---|
| $M_n$ (kg/mol) | 106.4 | 112.7 | 116.7 |
| $M_w/M_n$ | 1.06 | 1.14 | 1.14 |
| $T_g$ (° C.) | −38.1 | −38.7 | −40.6 |
| styrene content (%) | 21.8 | 21.5 | 20.5 |
| 1,2-linkage content (%) | 48.0 | 48.4 | 47.7 |

Examples 15-20: Filled Compositions

The polymers from Examples 12-14 were used with the formulation shown in Table 1c above to provide compositions from which vulcanizates designated as Examples 15-17 respectively below were prepared.

The same polymers were used with the formulation shown above in Table 1b to provide other compositions from which vulcanizates designated as Examples 18-20 below were prepared.

Mixing, vulcanization, and testing on these filled compositions were conducted similar to those described above in connection with Examples 6-11. Physical properties are summarized below in Table 5.

TABLE 5

Testing data from Examples 15-20

| | 15 | 16 | 17 | 18 | 19 | 20 |
|---|---|---|---|---|---|---|
| | | | Compound formulation | | | |
| | | Table 1c | | | Table 1b | |
| | | | Polymer used (example no.) | | | |
| | 12 | 13 | 14 | 12 | 13 | 14 |
| Shore A hardness @ 23° C. | 53.1 | 57.1 | 58.0 | 55.8 | 59.3 | 59.1 |
| Rebound @ 50° C. | 54.6 | 60.0 | 61.0 | 52.0 | 56.2 | 56.4 |
| Tensile testing, 23° C. | | | | | | |
| Modulus, 50% strain (MPa) | 1.305 | 1.691 | 1.695 | 1.595 | 1.943 | 1.900 |
| Modulus, 100% strain (MPa) | 2.217 | 3.390 | 3.514 | 2.694 | 3.793 | 3.784 |
| Modulus, 200% strain (MPa) | 5.343 | 8.367 | 9.156 | 5.350 | 7.899 | 8.336 |
| Modulus, 300% strain (MPa) | 9.978 | — | — | 9.102 | 13.06 | — |
| $T_b$ (MPa) | 12.5 | 13.7 | 13.6 | 10.6 | 15.6 | 12.3 |
| $E_b$ (%) | 345.1 | 293.1 | 270.6 | 331.4 | 343.7 | 274.6 |
| Temperature sweep, 10 Hz | | | | | | |
| Temp. at tan δ peak (° C.) | −22.87 | −22.35 | −23.59 | −19.96 | −19.87 | −20.05 |
| G' @ −20° C. and 0.20% strain (MPa) | 40.7 | 31.4 | 22.1 | 63.1 | 55.6 | 34.6 |
| Strain sweep, 60° C. and 10 Hz | | | | | | |
| G' @ 6.96% strain (MPa) | 1.91 | 2.18 | 2.08 | 1.99 | 2.28 | 2.18 |
| tan δ @ 6.96% strain | 0.110 | 0.0741 | 0.0702 | 0.115 | 0.0735 | 0.0730 |

The data from Table 5 display trends similar to those seen above in connection with Table 3.

Example 21: Synthesis of 3,4-bis(trimethylsilyloxy)benzaldehyde

To a dry flask was charged ~4.83 g 3,4-dihydroxybenzaldehyde, ~4.80 g imidazole, and 50 mL THF under nitrogen. The solution was cooled to −78° C. before ~43.8 mL of a 1.6 M solution of n-butyllithium was added in dropwise fashion.

The reaction mixture was warmed to room temperature before ~7.61 g chlorotrimethylsilane was added in dropwise fashion, and then the reaction mixture was stirred for ~2 hours at room temperature.

After LiCl precipitated to the bottom of the vessel, the ~0.33 M 3,4-bis(trimethyl-silyloxy)benzaldehyde (BTMSBA) was used immediately as a terminating compound in Examples 26-27 below.

Examples 22-27: Cis-1,4-polybutadienes

Catalysts were prepared by adding to dried, capped, N$_2$-flushed bottles the following ingredients:

TABLE 6

| Catalyst ingredients | | | | | |
|---|---|---|---|---|---|
| | | A | B | C | D |
| butadiene in hexane | % by wt. | 21.4 | 22.2 | 21.4 | 22.2 |
| | amount (g) | 1.6 | 3.0 | 3.6 | 3.6 |
| MAO (1.51M), mL | | 5.96 | 4.68 | 5.67 | 5.67 |
| neodymium versatate (0.050M), mL | | 5.15 | 4.04 | 4.90 | 4.90 |
| diisobutylaluminum hydride (1.0M), mL | | 5.40 | 4.24 | 5.14 | 5.14 |
| diethylaluminum chloride (1.0M), mL | | 1.03 | 0.81 | 0.98 | 0.98 |

The mixtures were aged for 15 minutes at room temperature prior to use in the following polymerizations.

To a N$_2$-purged reactor equipped with a stirrer was added 1.22 kg hexane and 2.86 kg butadiene solution (21.4% by wt. in hexane). The reactor was charged with the catalyst mixture A, and the jacket temperature was set to 60° C. The polymerization was allowed to continue for ~60 minutes. The polymer cement was cooled to room temperature before being quenched and drum dried as described previously. This is designated Example 22 below.

The foregoing polymerization was essentially repeated three more times. In the first, 1.32 kg hexane, 2.76 kg butadiene solution (22.2% by wt. in hexane), as well as catalyst mixture B were used. This is designated Example 23 below.

In the second, catalyst mixture C was used and, prior to coagulation, 0.5 M DEAB in toluene (1.25 mL per 100 g polymer cement) was added and allowed to react for ~30 minutes in a 65° C. water bath. This is designated Example 24 below.

In the third, 1.32 kg hexane, 2.76 kg butadiene solution (22.2% by wt. in hexane), as well as catalyst mixture D were used. Three separate portions of the polymer cement were transferred to bottles and processed as follows before being quenched and drum dried as described previously.

Example 25: 1.0 M BTBDMSBA (from Example 2) in hexane (0.3 mL per 100 g polymer cement) was added and permitted to react with the cement for ~30 min. in a 65° C. water bath before TBAF solution (1.0 M in THF, 0.7 mL per 100 g polymer cement) was added, and the bottle was rotated in a 25° C. water bath for ~4 hours.

Example 26: 0.33 M BTMSBA (from Example 21) in hexane (0.91 mL per 100 g polymer cement) was added and permitted to react with the cement for ~30 min. in a 65° C. water bath.

Example 27: 0.33 M BTMSBA (from Example 21) in hexane (0.91 mL per 100 g polymer cement) was added and permitted to react with the cement for ~30 min. in a 65° C. water bath before 1.0 M HCl in isopropanol (1.0 mL per 100 g polymer cement) was added, and the bottle was rotated in a 50° C. water bath for ~30 min.

The properties of these polybutadienes are summarized in the following table. As before, molecular weights were determined by GPC, but the microstructure of the polymers was determined by IR spectroscopic analysis. Cold flow resistance values were determined as described above.

TABLE 7

Properties of polymers from Examples 22-27

|  | 22 | 23 | 24 | 25 | 26 | 27 |
|---|---|---|---|---|---|---|
| $M_n$ (kg/mol) | 117.8 | 132.9 | 117.4 | 121.3 | 108.6 | 120.5 |
| $M_w/M_n$ | 2.14 | 2.18 | 2.16 | 2.22 | 2.49 | 2.25 |
| $ML_{1+4}$ @ 100° C. | 28.2 | 45.7 | 27.9 | 41.6 | 50.6 | 33.7 |
| cold flow (mm) | 1.94 | 2.34 | 1.93 | 2.62 | 2.98 | 2.25 |
| cis 1,4-linkage content (%) | 94.8 | 96.7 | 94.9 | 95.2 | 95.6 | 95.3 |
| trans 1,4-linkage content (%) | 4.6 | 2.8 | 4.6 | 4.3 | 3.9 | 4.2 |
| 1,2-linkage content (%) | 0.6 | 0.5 | 0.6 | 0.5 | 0.5 | 0.5 |

Examples 28-33: Filled Compositions

The polymers from Examples 22-27 were used with the formulation shown above in Table 1d to provide compositions from which were prepared vulcanizates designated, respectively, as Examples 28-33 below.

Mixing, vulcanization, and testing on these filled compositions were conducted similar to those described above in connection with Examples 6-11, with physical properties summarized in the following table.

TABLE 8

Testing data from Examples 28-33

|  | 28 | 29 | 30 | 31 | 32 | 33 |
|---|---|---|---|---|---|---|
|  | \multicolumn{6}{c}{Polymer used (example no.)} |
|  | 22 | 23 | 24 | 25 | 26 | 27 |
| $ML_{1+4}$ @ 130° C. | 53.5 | 71.2 | 54.9 | 70.7 | 65.0 | 60.5 |
| Tensile testing, 23° C. | | | | | | |
| Modulus, 300% strain (MPa) | 10.48 | 10.61 | 10.24 | 11.27 | 10.72 | 10.74 |
| $T_b$ (MPa) | 17.87 | 18.76 | 14.30 | 14.01 | 13.98 | 14.64 |
| $E_b$ (%) | 447 | 456 | 383 | 354 | 365 | 377 |
| tan δ @ 50° C., 3% strain, 15 Hz | 0.1315 | 0.1137 | 0.1120 | 0.1013 | 0.1029 | 0.1034 |
| Dynastat tan δ, 50° C. and 10 Hz | 0.1123 | 0.0993 | 0.1008 | 0.0896 | 0.0885 | 0.0911 |

The data of Table 8 show, inter alia, that vulcanizates made with cis-1,4-polybutadienes functionalized with aryl groups that include hydroxyl substituents directly bonded to adjacent ring carbon atoms (Examples 31-33) exhibit fairly significant reductions in tan δ at 50° C. (corresponding to reductions in hysteresis) relative to vulcanizates made from non-functionalized control polymers (Examples 28-29) or even from a comparative functionalized polymer (Example 30).

B. Examples 34-50 (Initiators)

Butadiene solutions (all in hexane), styrene (33% in hexane), hexane, n-butyllithium (n-BuLi, 1.60 M in hexane), 2,2-bis(2'-tetrahydrofuryl)propane (1.6 M solution in hexane, stored over $CaH_2$), and butylated hydroxytoluene (BHT) solution in hexane were used in these examples.

Commercially available reagents and starting materials included the following, all of which were used without further purification unless otherwise noted in a specific example:

from Sigma-Aldrich Co.—3,4-dihydroxybenzaldehyde (97%), 1,3-propanedithiol (99%), p-toluenesulfonic acid monohydrate (98.5%), ethyl acetate (99.5%), and 4-di(methylamino)pyridine (DMAP, 99%), and from ACROS Organics—tert-butyldimethylsilyl chloride (98%) and TBAF (1 M in THF, containing ~5% water).

Testing was performed on filled compositions made according to the formulations shown in Tables 9a (a formulation employing only silica as a particulate filler) and 9b (a formulation employing only carbon black as a particulate filler).

TABLE 9a

Composition for vulcanizates, silica filler

| | Amount (phr) |
|---|---|
| Masterbatch | |
| synthesized polymer | 80 |
| poly(isoprene) (natural rubber) | 20 |
| silica | 52.5 |
| wax | 2 |
| N-phenyl-N'-(1,3-dimethylbutyl)-p-phenylenediamine | 0.95 |
| stearic acid | 2 |
| black oil | 10 |
| Re-mill | |
| silica | 2.5 |
| silane | 5 |
| Final | |
| sulfur | 1.5 |
| ZnO | 2.5 |
| 2,2'-dithiobisbenzothiazole | 2.0 |
| N-t-butylbenzothiazole-2-sulfenamide | 0.7 |
| N,N'-diphenylguanidine | 1.4 |
| TOTAL | 183.05 |

TABLE 9b

Composition for vulcanizates, carbon black filler

| | Amount (phr) |
|---|---|
| Masterbatch | |
| synthesized polymer | 100 |
| carbon black (N343 type) | 50 |
| wax | 2 |
| N-phenyl-N'-(1,3-dimethylbutyl)-p-phenylenediamine | 0.95 |
| stearic acid | 2 |
| black oil | 10 |
| Final | |
| sulfur | 1.5 |
| ZnO | 2.5 |
| 2,2'-dithiobisbenzothiazole | 0.5 |
| N-t-butylbenzothiazole-2-sulfenamide | 0.5 |
| N,N'-diphenylguanidine | 0.3 |
| TOTAL | 170.25 |

Example 34: 3,4-di(tert-butyldimethylsiloxy)phenyl-1,3-dithiane

To a dried 500 mL flask including a magnetic stirring bar and a reflux condenser was added 8.2 g 3,4-dihydroxybenzaldehyde, 1.6 g p-toluenesulfonic acid monohydrate, and 100 mL THF, followed by 6 mL 1,3-propanedithiol in 30 mL THF. This mixture was refluxed under nitrogen for ~12 hours. After cooling to room temperature, the mixture was filtered, with the filtrate being washed twice with saturated NaHCO$_3$ (100 mL) and once with saturated NaCl solution (100 mL) before being dried over anhydrous MgSO$_4$. Solvent was evaporated, and the residue was purified using silica gel column chromatography using 50% ethyl acetate in hexane as eluting solvent. An oily product (13.3 g, 99% yield) was obtained, and $^1$H and $^{13}$C NMR in CDCl$_3$ confirmed the structure as

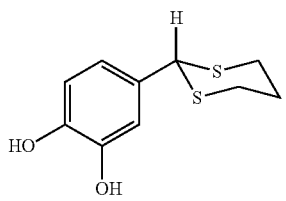 [SMILES: Oc1ccc(C2SCCCS2)cc1O]

To a dried 500 mL flask including a magnetic stirring bar was added 13.3 g of this dithiane, 0.5 g DMAP, 100 mL THF, and 30 mL triethylamine, followed by syringe addition of a solution of 18.7 g tert-butyldimethylsilyl chloride in 50 mL THF. This mixture was allowed to stir (under nitrogen) at room temperature for about an hour. Solid was filtered out of the mixture, and solvent was evaporated before the filtrate was purified using silica gel column chromatography using 5% ethyl acetate in hexane as eluting solvent. A white solid (24.9 g, 92% yield) was obtained, and $^1$H and $^{13}$C NMR in CDCl$_3$ confirmed this product to be 3,4-di(tert-butyldimethylsiloxy)phenyl-1,3-dithiane.

The 3,5-, 2,5-, 2,3-, etc., analogs of 3,4-di(tert-butyldimethylsiloxy)phenyl-1,3-dithiane can be prepared similarly, using the corresponding dihydroxybenzaldehydes. Also, 4-(tert-butyldimethylsiloxy)phenyl-1,3-dithiane can be prepared by using 4-hydroxybenzaldehyde as a starting material. All of the benzaldehydes can be obtained from a commercial supplier such as, for example, Sigma-Aldrich.

Example 35: BTBDMSBA (Alternative to Synthesis from Example 2)

To a dried 500 mL flask including a magnetic stirring bar was added ~8.2 g 3,4-dihydroxybenzaldehyde, ~0.5 g DMAP, 100 mL THF, and 30 mL triethylamine, followed by syringe addition of a solution of ~19.0 g tert-butyldimethylsilyl chloride in 50 mL THF. This mixture was allowed to stir (under nitrogen) at room temperature for about an hour. Solid was filtered out of the mixture, and solvent was evaporated before the filtrate was purified using silica gel column chromatography using 10% ethyl acetate in hexane as eluting solvent. A waxy, oily semi-solid (21.3 g, 97% yield) was obtained. $^1$H and $^{13}$C NMR confirmed the product to be BTBDMSBA.

Example 36: SBR (Control)

To a N$_2$-purged reactor equipped with a stirrer was added 1.47 kg hexane, 0.41 kg styrene solution, and 2.60 kg butadiene solution (20.9% in hexane). The reactor was charged with ~3.2 mL n-BuLi solution followed by 1.1 mL 2,2-bis(2'-tetrahydrofuryl)propane solution. The reactor jacket was heated to 50° C. and, after ~30 minutes, the batch temperature peaked at ~64° C. After an additional ~30 minutes, the polymer cement was dropped into isopropanol containing BHT and drum dried.

This polymer is designated sample 36 in Table 10 below.

Examples 37-40: 3,4-di(tert-butyldimethylsiloxy)phenyl-1,3-dithiane as Initiator Precursor To a N$_2$-purged reactor similar to that employed in Example 36 was added 1.37 kg hexane, 0.41 kg styrene solution, and 2.71 kg butadiene solution (20.1% in hexane). The reactor was charged with 5.9 mL of a 1.0 M solution of the dithiane from Example 34 in hexane followed by 3.9 mL n-BuLi solution. After ~5 minutes, 1.1 mL 2,2-bis(2'-tetrahydro-furyl)propane solution was added. The reactor jacket was heated to 50° C. and, after ~35 minutes, the batch temperature peaked at ~67° C.

After an additional ~30 minutes, portions of the polymer cement were transferred to glass bottles and terminated with

- samples 37 and 38—isopropanol,
- sample 39—BTBDMSBA (from Example 35), 1.0 M in hexane (using a 1:1 ratio of benzaldehyde to Li atoms), and
- sample 40—SnCl$_4$, 0.25 M in hexane (using a 1:1 ratio of Sn to Li).

Each sample was agitated for an additional ~30 min. in a 50° C. water bath. The protecting groups from samples 5-7 were hydrolyzed by reaction at room temperature (~2 hours) with TBAF solution (~20% molar excess relative to calculated amount of protecting groups).

Each polymer cement was coagulated and dried as in Example 36.

Properties of the polymers from Examples 36-40 are summarized below in Table 10, where M$_p$ represents peak molecular weight.

TABLE 10

| Polymer properties | | | | | |
|---|---|---|---|---|---|
| | 36 | 37 | 38 | 39 | 40 |
| $M_n$ (kg/mol) | 134 | 98 | 99 | 102 | 137 |
| $M_p$ (kg/mol) | 144 | 103 | 103 | 103 | 109 |
| $M_w/M_n$ | 1.05 | 1.11 | 1.14 | 1.18 | 2.18 |
| $T_g$ (° C.) | −37.7 | −41.0 | −41.1 | −40.8 | −41.4 |
| % coupling | 0 | 5.0 | 5.0 | 14.9 | broad |

Sample 39 showed excellent cold flow results when subjected to the testing procedure described above.

Examples 41-49: Preparation and Testing of Vulcanizates

Using the formulations from Table 9a and 9b above, vulcanizable elastomeric compounds containing reinforcing fillers were prepared from samples 36-40. Those prepared from the Table 9a formulation are denominated Examples 41-45 respectively, while those prepared from the Table 9b formulation are denominated Examples 46-50 respectively. Compounds were cured for ~15 minutes at 171° C.

Strain sweep test results are tabulated in Tables 11a and 11b, while temperature sweep test results are tabulated in Tables 12a and 12b.

TABLE 11a

| Results of strain sweep testing @ 60° C., Examples 41-45 | | | | | | | | | | |
|---|---|---|---|---|---|---|---|---|---|---|
| Strain | 41 (sample 36) | | 42 (sample 37) | | 43 (sample 38) | | 44 (sample 39) | | 45 (sample 40) | |
| (%) | tan δ | G' (MPa) | tan δ | G' (MPa) | tan δ | G' (MPa) | tan δ | G' (MPa) | tan δ | G' (MPa) |
| 0.249 | 0.0706 | 8.25 | 0.0648 | 7.79 | 0.0621 | 3.88 | 0.0449 | 3.42 | 0.0481 | 3.75 |
| 0.497 | 0.0859 | 7.73 | 0.0790 | 7.32 | 0.0676 | 3.79 | 0.0475 | 3.37 | 0.0514 | 3.69 |
| 0.745 | 0.0983 | 7.26 | 0.0917 | 6.87 | 0.0741 | 3.69 | 0.0508 | 3.32 | 0.0551 | 3.63 |
| 0.994 | 0.1081 | 6.88 | 0.1011 | 6.50 | 0.0795 | 3.59 | 0.0543 | 3.27 | 0.0579 | 3.57 |
| 1.243 | 0.1155 | 6.56 | 0.1082 | 6.21 | 0.0840 | 3.51 | 0.0573 | 3.22 | 0.0605 | 3.51 |
| 1.491 | 0.1208 | 6.30 | 0.1137 | 5.97 | 0.0877 | 3.43 | 0.0598 | 3.17 | 0.0627 | 3.46 |
| 1.739 | 0.1249 | 6.08 | 0.1182 | 5.76 | 0.0906 | 3.37 | 0.0620 | 3.13 | 0.0646 | 3.41 |
| 1.986 | 0.1282 | 5.89 | 0.1217 | 5.58 | 0.0930 | 3.31 | 0.0639 | 3.09 | 0.0662 | 3.37 |
| 2.238 | 0.1306 | 5.72 | 0.1247 | 5.42 | 0.0950 | 3.25 | 0.0654 | 3.05 | 0.0676 | 3.34 |
| 2.486 | 0.1329 | 5.57 | 0.1272 | 5.28 | 0.0965 | 3.20 | 0.0667 | 3.02 | 0.0688 | 3.30 |
| 2.734 | 0.1345 | 5.44 | 0.1292 | 5.15 | 0.0979 | 3.16 | 0.0678 | 2.99 | 0.0696 | 3.27 |
| 2.982 | 0.1361 | 5.32 | 0.1310 | 5.03 | 0.0992 | 3.12 | 0.0687 | 2.96 | 0.0705 | 3.23 |
| 3.231 | 0.1375 | 5.20 | 0.1324 | 4.92 | 0.1000 | 3.08 | 0.0694 | 2.93 | 0.0713 | 3.20 |
| 3.482 | 0.1385 | 5.10 | 0.1338 | 4.82 | 0.1007 | 3.04 | 0.0699 | 2.91 | 0.0718 | 3.18 |
| 3.729 | 0.1396 | 5.00 | 0.1350 | 4.73 | 0.1013 | 3.01 | 0.0705 | 2.88 | 0.0723 | 3.15 |
| 3.977 | 0.1406 | 4.91 | 0.1361 | 4.64 | 0.1020 | 2.97 | 0.0709 | 2.86 | 0.0726 | 3.12 |
| 4.225 | 0.1412 | 4.82 | 0.1368 | 4.56 | 0.1024 | 2.94 | 0.0713 | 2.84 | 0.0730 | 3.10 |
| 4.477 | 0.1418 | 4.74 | 0.1376 | 4.48 | 0.1028 | 2.91 | 0.0714 | 2.82 | 0.0732 | 3.08 |
| 4.725 | 0.1424 | 4.66 | 0.1385 | 4.41 | 0.1031 | 2.88 | 0.0718 | 2.80 | 0.0735 | 3.06 |
| 4.972 | 0.1430 | 4.59 | 0.1391 | 4.34 | 0.1033 | 2.86 | 0.0718 | 2.78 | 0.0736 | 3.03 |
| 5.469 | 0.1439 | 4.46 | 0.1400 | 4.21 | 0.1036 | 2.81 | 0.0722 | 2.74 | 0.0739 | 2.99 |
| 5.968 | 0.1444 | 4.33 | 0.1406 | 4.09 | 0.1040 | 2.76 | 0.0724 | 2.71 | 0.0741 | 2.96 |
| 6.464 | 0.1448 | 4.22 | 0.1412 | 3.98 | 0.1042 | 2.72 | 0.0724 | 2.68 | 0.0742 | 2.92 |
| 6.964 | 0.1453 | 4.11 | 0.1415 | 3.88 | 0.1041 | 2.68 | 0.0725 | 2.65 | 0.0742 | 2.89 |
| 7.460 | 0.1453 | 4.01 | 0.1416 | 3.78 | 0.1043 | 2.64 | 0.0728 | 2.62 | 0.0743 | 2.86 |
| 7.962 | 0.1455 | 3.92 | 0.1418 | 3.69 | 0.1043 | 2.60 | 0.0727 | 2.59 | 0.0741 | 2.82 |
| 8.458 | 0.1454 | 3.84 | 0.1419 | 3.61 | 0.1040 | 2.57 | 0.0727 | 2.57 | 0.0741 | 2.80 |
| 8.958 | 0.1453 | 3.76 | 0.1416 | 3.53 | 0.1039 | 2.53 | 0.0726 | 2.54 | 0.0740 | 2.77 |
| 9.453 | 0.1452 | 3.69 | 0.1415 | 3.46 | 0.1036 | 2.50 | 0.0726 | 2.52 | 0.0737 | 2.74 |
| 9.950 | 0.1449 | 3.61 | 0.1412 | 3.39 | 0.1033 | 2.47 | 0.0723 | 2.49 | 0.0738 | 2.71 |
| 10.449 | 0.1448 | 3.55 | 0.1408 | 3.33 | 0.1031 | 2.44 | 0.0722 | 2.47 | 0.0736 | 2.69 |
| 10.946 | 0.1444 | 3.48 | 0.1405 | 3.27 | 0.1028 | 2.41 | 0.0721 | 2.45 | 0.0734 | 2.67 |
| 11.446 | 0.1440 | 3.42 | 0.1401 | 3.21 | 0.1026 | 2.39 | 0.0720 | 2.43 | 0.0733 | 2.64 |
| 11.943 | 0.1435 | 3.37 | 0.1397 | 3.16 | 0.1023 | 2.36 | 0.0717 | 2.41 | 0.0731 | 2.62 |
| 12.442 | 0.1433 | 3.31 | 0.1393 | 3.10 | 0.1020 | 2.34 | 0.0717 | 2.39 | 0.0730 | 2.60 |
| 12.940 | 0.1427 | 3.26 | 0.1390 | 3.06 | 0.1017 | 2.31 | 0.0715 | 2.37 | 0.0727 | 2.58 |
| 13.439 | 0.1422 | 3.21 | 0.1383 | 3.01 | 0.1013 | 2.29 | 0.0713 | 2.35 | 0.0726 | 2.56 |
| 13.933 | 0.1416 | 3.16 | 0.1377 | 2.96 | 0.1011 | 2.27 | 0.0712 | 2.33 | 0.0724 | 2.53 |
| 14.432 | 0.1415 | 3.12 | 0.1373 | 2.92 | 0.1008 | 2.24 | 0.0710 | 2.31 | 0.0722 | 2.51 |

TABLE 11b

| Results of strain sweep testing @ 60° C., Examples 46-50 | | | | | | | | | | |
|---|---|---|---|---|---|---|---|---|---|---|
| Strain | 46 (sample 36) | | 47 (sample 37) | | 48 (sample 38) | | 49 (sample 39) | | 50 (sample 40) | |
| (%) | tan δ | G' (MPa) | tan δ | G' (MPa) | tan δ | G' (MPa) | tan δ | G' (MPa) | tan δ | G' (MPa) |
| 0.249 | 0.1046 | 5.72 | 0.0936 | 5.60 | 0.0872 | 3.36 | 0.0663 | 3.16 | 0.0702 | 3.18 |
| 0.497 | 0.1336 | 5.23 | 0.1176 | 5.20 | 0.0920 | 3.27 | 0.0706 | 3.10 | 0.0726 | 3.12 |
| 0.746 | 0.1584 | 4.81 | 0.1393 | 4.83 | 0.1000 | 3.18 | 0.0758 | 3.04 | 0.0769 | 3.07 |

TABLE 11b-continued

Results of strain sweep testing @ 60° C., Examples 46-50

| Strain (%) | 46 (sample 36) tan δ | G' (MPa) | 47 (sample 37) tan δ | G' (MPa) | 48 (sample 38) tan δ | G' (MPa) | 49 (sample 39) tan δ | G' (MPa) | 50 (sample 40) tan δ | G' (MPa) |
|---|---|---|---|---|---|---|---|---|---|---|
| 0.995 | 0.1769 | 4.48 | 0.1584 | 4.51 | 0.1096 | 3.09 | 0.0819 | 2.98 | 0.0810 | 3.02 |
| 1.243 | 0.1902 | 4.22 | 0.1705 | 4.27 | 0.1155 | 3.01 | 0.0857 | 2.92 | 0.0848 | 2.96 |
| 1.490 | 0.1999 | 4.01 | 0.1805 | 4.07 | 0.1197 | 2.94 | 0.0899 | 2.88 | 0.0890 | 2.92 |
| 1.741 | 0.2070 | 3.85 | 0.1880 | 3.90 | 0.1239 | 2.89 | 0.0922 | 2.84 | 0.0924 | 2.87 |
| 1.987 | 0.2124 | 3.70 | 0.1950 | 3.75 | 0.1286 | 2.83 | 0.0949 | 2.79 | 0.0945 | 2.83 |
| 2.238 | 0.2163 | 3.58 | 0.1990 | 3.63 | 0.1313 | 2.78 | 0.0972 | 2.76 | 0.0973 | 2.79 |
| 2.485 | 0.2191 | 3.47 | 0.2024 | 3.53 | 0.1333 | 2.74 | 0.0994 | 2.73 | 0.0997 | 2.75 |
| 2.736 | 0.2211 | 3.38 | 0.2055 | 3.43 | 0.1352 | 2.70 | 0.1010 | 2.70 | 0.1020 | 2.72 |
| 2.984 | 0.2224 | 3.30 | 0.2073 | 3.35 | 0.1370 | 2.66 | 0.1019 | 2.67 | 0.1038 | 2.69 |
| 3.234 | 0.2232 | 3.22 | 0.2090 | 3.27 | 0.1381 | 2.63 | 0.1030 | 2.65 | 0.1049 | 2.66 |
| 3.481 | 0.2235 | 3.15 | 0.2094 | 3.21 | 0.1391 | 2.60 | 0.1035 | 2.62 | 0.1069 | 2.63 |
| 3.732 | 0.2237 | 3.09 | 0.2101 | 3.15 | 0.1390 | 2.58 | 0.1041 | 2.60 | 0.1080 | 2.61 |
| 3.978 | 0.2235 | 3.04 | 0.2111 | 3.09 | 0.1412 | 2.55 | 0.1048 | 2.58 | 0.1088 | 2.58 |
| 4.227 | 0.2232 | 2.99 | 0.2111 | 3.04 | 0.1408 | 2.52 | 0.1049 | 2.56 | 0.1100 | 2.56 |
| 4.479 | 0.2226 | 2.94 | 0.2099 | 2.99 | 0.1415 | 2.50 | 0.1051 | 2.55 | 0.1102 | 2.54 |
| 4.723 | 0.2219 | 2.90 | 0.2096 | 2.95 | 0.1416 | 2.48 | 0.1056 | 2.53 | 0.1115 | 2.52 |
| 4.972 | 0.2212 | 2.86 | 0.2101 | 2.91 | 0.1418 | 2.46 | 0.1045 | 2.51 | 0.1123 | 2.50 |
| 5.474 | 0.2194 | 2.78 | 0.2093 | 2.83 | 0.1414 | 2.42 | 0.1053 | 2.49 | 0.1127 | 2.46 |
| 5.970 | 0.2174 | 2.72 | 0.2072 | 2.77 | 0.1415 | 2.39 | 0.1054 | 2.46 | 0.1128 | 2.43 |
| 6.471 | 0.2153 | 2.66 | 0.2055 | 2.71 | 0.1415 | 2.36 | 0.1049 | 2.43 | 0.1135 | 2.40 |
| 6.965 | 0.2131 | 2.61 | 0.2025 | 2.66 | 0.1400 | 2.33 | 0.1041 | 2.41 | 0.1139 | 2.37 |
| 7.468 | 0.2109 | 2.56 | 0.2031 | 2.61 | 0.1396 | 2.30 | 0.1040 | 2.39 | 0.1130 | 2.34 |
| 7.964 | 0.2086 | 2.51 | 0.1988 | 2.57 | 0.1375 | 2.28 | 0.1031 | 2.37 | 0.1132 | 2.32 |
| 8.467 | 0.2066 | 2.47 | 0.1969 | 2.53 | 0.1383 | 2.26 | 0.1018 | 2.35 | 0.1130 | 2.30 |
| 8.958 | 0.2045 | 2.44 | 0.1959 | 2.49 | 0.1369 | 2.24 | 0.1020 | 2.34 | 0.1125 | 2.28 |
| 9.457 | 0.2025 | 2.40 | 0.1943 | 2.46 | 0.1360 | 2.22 | 0.1014 | 2.32 | 0.1122 | 2.26 |
| 9.951 | 0.2004 | 2.37 | 0.1909 | 2.43 | 0.1346 | 2.20 | 0.1005 | 2.30 | 0.1126 | 2.24 |
| 10.451 | 0.1986 | 2.34 | 0.1896 | 2.39 | 0.1345 | 2.18 | 0.0989 | 2.29 | 0.1115 | 2.22 |
| 10.950 | 0.1966 | 2.31 | 0.1879 | 2.37 | 0.1340 | 2.17 | 0.0991 | 2.28 | 0.1105 | 2.20 |
| 11.446 | 0.1949 | 2.29 | 0.1859 | 2.34 | 0.1336 | 2.15 | 0.0970 | 2.27 | 0.1104 | 2.19 |
| 11.947 | 0.1933 | 2.26 | 0.1838 | 2.32 | 0.1321 | 2.14 | 0.0970 | 2.25 | 0.1098 | 2.17 |
| 12.452 | 0.1915 | 2.24 | 0.1825 | 2.29 | 0.1307 | 2.12 | 0.0964 | 2.24 | 0.1094 | 2.16 |
| 12.949 | 0.1900 | 2.22 | 0.1803 | 2.27 | 0.1298 | 2.11 | 0.0964 | 2.23 | 0.1088 | 2.15 |
| 13.441 | 0.1885 | 2.19 | 0.1796 | 2.25 | 0.1296 | 2.10 | 0.0957 | 2.22 | 0.1084 | 2.13 |
| 13.944 | 0.1869 | 2.17 | 0.1777 | 2.23 | 0.1278 | 2.08 | 0.0953 | 2.21 | 0.1079 | 2.12 |
| 14.435 | 0.1855 | 2.15 | 0.1764 | 2.21 | 0.1286 | 2.07 | 0.0947 | 2.20 | 0.1070 | 2.11 |

TABLE 12a

Results (tan δ) of temperature sweep testing @ 2% strain, Examples 41-45

| Temp. (° C.) | 41 (sample 36) | 42 (sample 37) | 43 (sample 38) | 44 (sample 39) | 45 (sample 40) |
|---|---|---|---|---|---|
| −80.20 | 0.0187 | 0.0207 | 0.0201 | 0.0205 | 0.0324 |
| −74.01 | 0.0185 | 0.0201 | 0.0199 | 0.0195 | 0.0243 |
| −70.05 | 0.0191 | 0.0208 | 0.0209 | 0.0203 | 0.0234 |
| −66.01 | 0.0209 | 0.0231 | 0.0230 | 0.0225 | 0.0245 |
| −59.99 | 0.0308 | 0.0365 | 0.0373 | 0.0351 | 0.0345 |
| −55.97 | 0.0502 | 0.0601 | 0.0608 | 0.0569 | 0.0547 |
| −50.01 | 0.0829 | 0.0929 | 0.0829 | 0.0843 | 0.0848 |
| −45.99 | 0.0901 | 0.1047 | 0.0950 | 0.1003 | 0.0987 |
| −39.97 | 0.1239 | 0.1740 | 0.1882 | 0.1989 | 0.1851 |
| −36.00 | 0.2060 | 0.3244 | 0.3500 | 0.3656 | 0.3425 |
| −30.00 | 0.5200 | 0.7187 | 0.7458 | 0.7452 | 0.7535 |
| −25.98 | 0.7445 | 0.7871 | 0.8235 | 0.8275 | 0.8960 |
| −19.99 | 0.5936 | 0.5287 | 0.5819 | 0.6278 | 0.6999 |
| −16.00 | 0.4247 | 0.3918 | 0.4339 | 0.4885 | 0.5450 |
| −9.95 | 0.2718 | 0.2666 | 0.2951 | 0.3404 | 0.3766 |
| −4.94 | 0.3203 | 0.3359 | 0.3527 | 0.3707 | 0.3752 |
| 0.07 | 0.2603 | 0.2796 | 0.2890 | 0.2958 | 0.2903 |
| 5.07 | 0.2203 | 0.2395 | 0.2443 | 0.2415 | 0.2300 |
| 10.04 | 0.1943 | 0.2120 | 0.2140 | 0.2029 | 0.1890 |
| 15.10 | 0.1767 | 0.1931 | 0.1931 | 0.1755 | 0.1605 |
| 20.10 | 0.1655 | 0.1801 | 0.1782 | 0.1551 | 0.1402 |
| 25.09 | 0.1569 | 0.1700 | 0.1665 | 0.1389 | 0.1252 |
| 30.01 | 0.1509 | 0.1622 | 0.1575 | 0.1258 | 0.1133 |
| 35.15 | 0.1457 | 0.1558 | 0.1503 | 0.1154 | 0.1036 |
| 40.07 | 0.1407 | 0.1492 | 0.1430 | 0.1058 | 0.0952 |
| 45.14 | 0.1351 | 0.1429 | 0.1357 | 0.0985 | 0.0883 |
| 50.10 | 0.1303 | 0.1375 | 0.1294 | 0.0916 | 0.0821 |
| 55.07 | 0.1265 | 0.1329 | 0.1237 | 0.0864 | 0.0774 |
| 60.12 | 0.1228 | 0.1290 | 0.1199 | 0.0828 | 0.0738 |
| 65.09 | 0.1192 | 0.1256 | 0.1161 | 0.0799 | 0.0710 |
| 70.10 | 0.1156 | 0.1220 | 0.1131 | 0.0771 | 0.0686 |
| 75.10 | 0.1128 | 0.1189 | 0.1101 | 0.0751 | 0.0661 |
| 80.06 | 0.1097 | 0.1160 | 0.1074 | 0.0735 | 0.0640 |
| 85.10 | 0.1072 | 0.1134 | 0.1046 | 0.0714 | 0.0623 |
| 90.13 | 0.1046 | 0.1109 | 0.1024 | 0.0699 | 0.0606 |
| 95.11 | 0.1026 | 0.1090 | 0.0997 | 0.0687 | 0.0590 |
| 100.12 | 0.1002 | 0.1072 | 0.0974 | 0.0672 | 0.0579 |

TABLE 12b

Results (tan δ) of temperature sweep testing @ 2% strain, Examples 46-50

| Temp. (° C.) | 46 (sample 36) | 47 (sample 37) | 48 (sample 38) | 49 (sample 39) | 50 (sample 40) |
|---|---|---|---|---|---|
| −78.44 | 0.0182 | 0.0187 | 0.0165 | 0.0159 | 0.0187 |
| −74.09 | 0.0170 | 0.0165 | 0.0158 | 0.0154 | 0.0173 |
| −70.14 | 0.0167 | 0.0164 | 0.0160 | 0.0158 | 0.0170 |
| −64.26 | 0.0168 | 0.0169 | 0.0168 | 0.0164 | 0.0176 |
| −60.66 | 0.0169 | 0.0177 | 0.0173 | 0.0171 | 0.0185 |
| −56.74 | 0.0180 | 0.0190 | 0.0189 | 0.0186 | 0.0200 |
| −50.59 | 0.0213 | 0.0240 | 0.0243 | 0.0244 | 0.0250 |
| −44.91 | 0.0309 | 0.0428 | 0.0440 | 0.0487 | 0.0462 |
| −40.68 | 0.0489 | 0.0921 | 0.0970 | 0.1099 | 0.1025 |
| −35.00 | 0.1647 | 0.3453 | 0.3715 | 0.4101 | 0.3844 |
| −30.72 | 0.3787 | 0.6395 | 0.6771 | 0.7364 | 0.7090 |
| −24.91 | 0.7538 | 0.7431 | 0.8122 | 0.8955 | 0.9322 |
| −19.25 | 0.6686 | 0.5047 | 0.5749 | 0.6696 | 0.7222 |
| −14.94 | 0.5007 | 0.3779 | 0.4447 | 0.5288 | 0.5718 |
| −11.06 | 0.3779 | 0.2922 | 0.3472 | 0.4211 | 0.4543 |
| −9.02 | 0.3269 | 0.2580 | 0.3082 | 0.3707 | 0.4036 |
| −3.77 | 0.4069 | 0.3582 | 0.3678 | 0.3744 | 0.3829 |
| 1.09 | 0.3381 | 0.3070 | 0.3021 | 0.2904 | 0.2900 |
| 5.75 | 0.2935 | 0.2723 | 0.2583 | 0.2352 | 0.2304 |
| 10.52 | 0.2640 | 0.2525 | 0.2308 | 0.2005 | 0.1932 |
| 15.45 | 0.2485 | 0.2409 | 0.2142 | 0.1776 | 0.1690 |
| 20.34 | 0.2398 | 0.2338 | 0.2027 | 0.1609 | 0.1535 |
| 25.38 | 0.2341 | 0.2298 | 0.1942 | 0.1505 | 0.1424 |
| 30.21 | 0.2303 | 0.2274 | 0.1892 | 0.1404 | 0.1342 |
| 35.17 | 0.2277 | 0.2247 | 0.1829 | 0.1323 | 0.1272 |
| 40.28 | 0.2241 | 0.2213 | 0.1767 | 0.1239 | 0.1203 |
| 45.51 | 0.2194 | 0.2154 | 0.1706 | 0.1173 | 0.1140 |
| 50.51 | 0.2133 | 0.2093 | 0.1642 | 0.1112 | 0.1088 |
| 55.07 | 0.2076 | 0.2038 | 0.1594 | 0.1063 | 0.1045 |
| 59.99 | 0.2034 | 0.1995 | 0.1550 | 0.1026 | 0.1011 |
| 64.91 | 0.2004 | 0.1954 | 0.1507 | 0.0986 | 0.0975 |
| 70.23 | 0.1954 | 0.1921 | 0.1477 | 0.0953 | 0.0950 |
| 75.01 | 0.1917 | 0.1887 | 0.1442 | 0.0926 | 0.0940 |
| 80.03 | 0.1890 | 0.1851 | 0.1414 | 0.0900 | 0.0899 |
| 85.19 | 0.1850 | 0.1815 | 0.1368 | 0.0878 | 0.0871 |
| 90.21 | 0.1807 | 0.1784 | 0.1343 | 0.0858 | 0.0852 |
| 95.18 | 0.1767 | 0.1735 | 0.1306 | 0.0830 | 0.0825 |

Tables 11a, 11b, 12a and 12b show that vulcanizates employing functional initiator-initiated SBR interpolymers exhibit significant reductions in hysteresis relative to compounds employing a n-BuLi initiated control SBR and that this effect is enhanced when a functional group resulting from terminal functionalization also is present and/or the protecting groups have been hydrolyzed to provide hydroxyl groups. Similar positive trends can be seen in the G' data in Tables 11a and 11b.

A more complete set of physical performance data was obtained on Examples 41, 43-44, 46 and 48-49. This data is summarized below in Table 13.

TABLE 13

Compound and vulcanizate properties

| | 41 | 43 | 44 | 46 | 48 | 49 |
|---|---|---|---|---|---|---|
| | | | synthetic polymer (sample no.) | | | |
| | 36 | 38 | 39 | 36 | 38 | 39 |
| MDR2000 @ 171° C. (final) | | | | | | |
| ML (kg · cm) | 1.81 | 1.60 | 2.96 | 0.82 | 1.55 | 2.98 |
| MH (kg · cm) | 23.27 | 21.98 | 22.58 | 16.64 | 18.05 | 18.24 |
| $t_{90}$ (min) | 7.32 | 4.82 | 4.29 | 5.88 | 6.72 | 8.16 |
| $ML_{1+4}$ @ 100° C. (final) | 17.0 | 33.3 | 88.1 | 21.3 | 45.2 | 104.0 |
| Tensile @ 23° C. (final, unaged) | | | | | | |
| $M_{50}$ (MPa) | 1.84 | 1.44 | 1.40 | 1.74 | 1.52 | 1.62 |
| $M_{300}$ (MPa) | 11.86 | 13.80 | 15.45 | 11.51 | 14.78 | 18.35 |
| $T_b$ (MPa) | 12.0 | 17.2 | 17.1 | 18.0 | 21.1 | 21.2 |
| $E_b$ (%) | 328 | 341 | 332 | 471 | 387 | 358 |
| Tensile @ 100° C. (final, unaged) | | | | | | |
| $M_{50}$ (MPa) | 1.71 | 1.45 | 1.48 | 1.36 | 1.45 | 1.53 |
| $M_{200}$ (MPa) | 6.43 | 7.25 | 6.69 | 5.90 | 7.66 | 8.82 |
| $T_b$ (MPa) | 6.8 | 7.5 | 6.8 | 8.4 | 10.1 | 10.3 |
| $E_b$ (%) | 196 | 201 | 183 | 278 | 270 | 225 |
| Strain sweep (60° C., 10 Hz, final) | | | | | | |
| G' @ 5% strain (MPa) | 4.502 | 2.855 | 2.778 | 2.880 | 2.903 | 2.513 |
| G" @ 5% strain (MPa) | 0.698 | 0.295 | 0.199 | 0.683 | 0.610 | 0.263 |
| tan δ | 0.1550 | 0.1033 | 0.0718 | 0.2373 | 0.2099 | 0.1045 |
| ΔG' (MPa) | 5.304 | 1.617 | 1.091 | 3.939 | 1.279 | 0.956 |
| Temp. sweep (2% strain, 10 Hz, final) | | | | | | |
| G' @ 0° C. (MPa) | 14.930 | 10.029 | 8.704 | 15.808 | 11.632 | 8.390 |
| G" @ 0° C. (MPa) | 4.783 | 2.904 | 2.593 | 6.110 | 3.685 | 2.645 |
| tan δ @ 0° C. (MPa) | 0.3183 | 0.2895 | 0.2976 | 0.3844 | 0.3152 | 0.3127 |

TABLE 13-continued

Compound and vulcanizate properties

| | 41 | 43 | 44 | 46 | 48 | 49 |
|---|---|---|---|---|---|---|
| | synthetic polymer (sample no.) | | | | | |
| | 36 | 38 | 39 | 36 | 38 | 39 |
| G' @ 60° C. (MPa) | 7.391 | 5.511 | 5.082 | 6.061 | 4.946 | 4.233 |
| G" @ 60° C. (MPa) | 1.029 | 0.662 | 0.421 | 1.355 | 0.767 | 0.437 |
| tan δ @ 60° C. (MPa) | 0.1392 | 0.1199 | 0.0829 | 0.2236 | 0.1551 | 0.1031 |
| Dynastat (60° C., final) | | | | | | |
| tan δ | 0.1161 | 0.0829 | 0.0553 | 0.2129 | 0.1285 | 0.0943 |
| Bound rubber (%) | 18.4 | 32.6 | 43.9 | 5.4 | 22.2 | 43.6 |

C. Examples 51-87 (Monomers)

Butadiene solutions (all in hexane), styrene solution (33% in hexane), hexane, n-butyllithium (n-BuLi, 1.60 M in hexane), 2,2-bis(2'-tetrahydrofuryl)propane (1.6 M solution in hexane, stored over $CaH_2$), and BHT solution in hexane used in these examples were from stock room inventory.

Commercially available reagents and starting materials included the following, all of which were used without further purification unless otherwise noted in a specific example:
  from Sigma-Aldrich Co.—2,3-dihydroxybenzaldehyde (97%), 3,4-dihydroxybenzaldehyde (97%), 3,5-dihydroxybenzaldehyde (98%), 2,5-dihydroxybenzaldehyde (98%), 3,4,5-trihydroxybenzaldehyde monohydrate (98%), methyltriphenylphosphenium bromide (MTP-Br, 98%), ethyl acetate (99.5%), and DMAP (99%), and
  from ACROS Organics—tert-butyldimethylsilyl chloride (98%) and TBAF (1 M in THF containing ~5% water).

Column chromatography was conducted using 200-425 mesh silica gel sorbent (Fisher Scientific; Pittsburgh, Pa.). Thin layer chromatography was performed on chromatography plates obtained from Sigma-Aldrich.

Testing was performed on vulcanizates made from rubber compounds according to the formulations shown in Tables 9a and 9b (see above).

Example 51: Synthesis of
3,4-di(tert-butyldimethylsiloxy)styrene

To a stirred, cold (0° C.) solution of 23.2 g MTP-Br in 100 mL dried THF under nitrogen was dropwise added 40.6 mL n-BuLi solution. After ~15 minutes, a solution of ~22.3 g BTBDMSBA (from Example 35) in 30 mL THF was dropwise added via syringe. The resulting yellow suspension was stirred for ~4 hours before being treated with $NH_4Cl$. This solution was filtered and concentrated under vacuum. The residue was purified by silica gel column chromatography using 5% ethyl acetate in hexane as the eluting solvent, resulting in collection of 20.6 g (94% yield) of a colorless oil. $^1H$ and $^{13}C$ NMR confirmed the compound to be 3,4-di(tert-butyldimethylsiloxy)styrene (DTBDMSOS).

Example 52: SBR (Control)

To a $N_2$-purged reactor equipped with a stirrer was added 0.81 kg hexane, 0.21 kg styrene solution, and 1.20 kg butadiene solution (22.6% in hexane). The reactor was charged with ~1.9 mL n-BuLi solution followed by 0.55 mL 2,2-bis(2'-tetrahydrofuryl)propane solution. The reactor jacket was heated to 50° C. and, after ~30 minutes, the batch temperature peaked at ~59° C.

After an additional ~30 minutes, the polymer cement was dropped into isopropanol containing BHT and drum dried. This polymer is designated sample 52 in Table 14 below.

Examples 53-55: Interpolymers including
3,4-di(tert-butyldimethylsiloxy)styrene Units A series of polymerizations in a $N_2$-purged reactor similar to that from Example 52 were conducted on mixtures including 0.81 kg hexane, 0.21 kg styrene solution, and 1.20 kg butadiene solution (22.6% in hexane). The mixtures differed in the amounts of DTBDMSOS (1.0 M in hexane) and n-BuLi solution employed, specifically,
  53—2.6 mL DTBDMSOS solution and 2.01 mL initiator,
  54—9.2 mL DTBDMSOS solution and 1.92 mL initiator, and
  55—14.3 mL DTBDMSOS solution and 1.80 mL initiator.

To each mixture also was added 0.55 mL 2,2-bis(2'-tetrahydrofuryl)propane solution. The reactor jacket was heated to 50° C. for each, and the batch temperature peaked at, respectively, ~56° C. (after ~32 minutes), ~57° C. (after ~30 minutes), and ~56° C. (after ~30 minutes). Sufficient TBAF solution was added so that the ratio of TBAF to DTBDMSOS for each was ~6:5, and these mixtures were agitated at room temperature for ~2 hours each.

Each of the polymer cements was dropped into isopropanol containing BHT and drum dried. These polymers are designated samples 53-55 in Table 14 below.

TABLE 14

Polymer properties

| | 52 | 53 | 54 | 55 |
|---|---|---|---|---|
| $M_n$ (kg/mol) | 107 | 102 | 108 | 119 |
| $M_p$ (kg/mol) | 112 | 105 | 111 | 122 |
| $M_w/M_n$ | 1.03 | 1.05 | 1.06 | 1.08 |
| $T_g$ (° C.) | -32.5 | -33.2 | -31.5 | -30.2 |
| % coupling | 1.41 | 3.05 | 4.90 | 7.10 |

Examples 56-58: Interpolymers Including
3,4-di(tert-butyldimethylsiloxy)styrene block To a $N_2$-purged reactor similar to that from Example 52 was added 1.55 kg hexane, 0.41 kg styrene solution, and 2.52 kg butadiene solution (21.6% in hexane). The reactor was charged with ~3.3 mL n-BuLi solution followed by 1.1 mL 2,2-bis(2'-tetrahydrofuryl)propane solution. The reactor jacket was heated to 50° C. and, after ~30 minutes, the batch temperature peaked at ~63° C.

After an additional ~30 minutes, portions of the polymer cement were dropped into glass bottles. Varying amounts of DTBDMSOS solution were added so as to provide, respectively, 1:1, 3:1 and 5:1 ratios of DTBDMSOS to Li atoms. These mixtures were agitated for an additional ~40 minutes in a 50° C. water bath.

TBAF solution was added so that the ratio of TBAF to DTBDMSOS for each was ~6:5, and these mixtures were agitated at room temperature for ~2 hours each.

Each of the polymer cements was dropped into isopropanol containing BHT and drum dried.

Example 59: Cold Flow Testing

Test samples were prepared and tested as described above.

Test results indicated that the sample prepared from the polymer of Example 53 was nearly identical in cold flow performance to the sample prepared from the polymer of Example 52, while samples prepared from the polymers of Examples 54 and 56-58 all were significantly better (~1.5× to ~3.5× greater) than the sample prepared from the polymer of Example 52, with the block interpolymers being better than the random interpolymers.

Examples 60-67: Preparation and Testing of Vulcanizates

Using the formulations from Table 9a and 9b above, vulcanizable elastomeric compounds containing reinforcing fillers were prepared from samples 52-55. Those prepared from the Table 9a formulation are denominated Examples 60-63 respectively, while those prepared from the Table 9b formulation are denominated Examples 64-67 respectively. Vulcanizates were prepared by curing these compounds for ~15 minutes at 171° C.

Strain sweep testing data is tabulated in Tables 15a (both G' and tan δ) and 15b (tan δ only), while temperature sweep test results are tabulated in Tables 16a and 16b.

TABLE 15a

Results of strain sweep testing (60° C., 10 Hz), Examples 60-63

| Strain | 60 (sample 52) | | 61 (sample 53) | | 62 (sample 54) | | 63 (sample 55) | |
|---|---|---|---|---|---|---|---|---|
| (%) | tan δ | G' (MPa) | tan δ | G' (MPa) | tan δ | G' (MPa) | tan δ | G' (MPa) |
| 0.249 | 0.0805 | 7.89 | 0.0868 | 7.28 | 0.0796 | 5.42 | 0.0714 | 5.32 |
| 0.497 | 0.0983 | 7.32 | 0.1066 | 6.70 | 0.0920 | 5.15 | 0.0808 | 5.11 |
| 0.746 | 0.1136 | 6.80 | 0.1232 | 6.21 | 0.1049 | 4.86 | 0.0914 | 4.89 |
| 0.994 | 0.1248 | 6.39 | 0.1348 | 5.82 | 0.1152 | 4.62 | 0.0998 | 4.70 |
| 1.243 | 0.1331 | 6.07 | 0.1428 | 5.53 | 0.1227 | 4.43 | 0.1064 | 4.53 |
| 1.491 | 0.1395 | 5.80 | 0.1485 | 5.29 | 0.1287 | 4.27 | 0.1113 | 4.39 |
| 1.739 | 0.1446 | 5.57 | 0.1527 | 5.09 | 0.1330 | 4.13 | 0.1152 | 4.28 |
| 1.988 | 0.1486 | 5.38 | 0.1558 | 4.92 | 0.1365 | 4.01 | 0.1182 | 4.17 |
| 2.237 | 0.1518 | 5.21 | 0.1580 | 4.78 | 0.1391 | 3.90 | 0.1204 | 4.08 |
| 2.486 | 0.1542 | 5.06 | 0.1597 | 4.65 | 0.1415 | 3.81 | 0.1223 | 3.99 |
| 2.735 | 0.1564 | 4.93 | 0.1609 | 4.53 | 0.1432 | 3.73 | 0.1240 | 3.92 |
| 2.984 | 0.1583 | 4.80 | 0.1618 | 4.43 | 0.1444 | 3.66 | 0.1250 | 3.85 |
| 3.233 | 0.1597 | 4.69 | 0.1624 | 4.34 | 0.1457 | 3.59 | 0.1259 | 3.79 |
| 3.482 | 0.1609 | 4.59 | 0.1628 | 4.25 | 0.1465 | 3.52 | 0.1267 | 3.73 |
| 3.731 | 0.1621 | 4.49 | 0.1631 | 4.18 | 0.1471 | 3.47 | 0.1273 | 3.67 |
| 3.976 | 0.1629 | 4.40 | 0.1631 | 4.10 | 0.1479 | 3.41 | 0.1277 | 3.62 |
| 4.225 | 0.1637 | 4.32 | 0.1630 | 4.04 | 0.1480 | 3.36 | 0.1279 | 3.58 |
| 4.474 | 0.1644 | 4.24 | 0.1629 | 3.97 | 0.1483 | 3.31 | 0.1280 | 3.53 |
| 4.723 | 0.1650 | 4.17 | 0.1628 | 3.92 | 0.1487 | 3.27 | 0.1282 | 3.49 |
| 4.973 | 0.1652 | 4.10 | 0.1627 | 3.86 | 0.1489 | 3.23 | 0.1283 | 3.45 |
| 5.470 | 0.1660 | 3.97 | 0.1622 | 3.76 | 0.1490 | 3.15 | 0.1284 | 3.37 |
| 5.967 | 0.1665 | 3.86 | 0.1614 | 3.67 | 0.1490 | 3.07 | 0.1284 | 3.30 |
| 6.466 | 0.1666 | 3.75 | 0.1605 | 3.58 | 0.1490 | 3.01 | 0.1283 | 3.24 |
| 6.965 | 0.1667 | 3.65 | 0.1599 | 3.50 | 0.1488 | 2.95 | 0.1280 | 3.18 |
| 7.465 | 0.1667 | 3.56 | 0.1591 | 3.43 | 0.1485 | 2.89 | 0.1277 | 3.12 |
| 7.958 | 0.1666 | 3.48 | 0.1583 | 3.36 | 0.1483 | 2.84 | 0.1273 | 3.06 |
| 8.458 | 0.1663 | 3.40 | 0.1573 | 3.30 | 0.1479 | 2.79 | 0.1270 | 3.01 |
| 8.955 | 0.1660 | 3.32 | 0.1565 | 3.24 | 0.1475 | 2.74 | 0.1264 | 2.97 |
| 9.454 | 0.1656 | 3.26 | 0.1558 | 3.18 | 0.1470 | 2.69 | 0.1259 | 2.92 |
| 9.954 | 0.1654 | 3.19 | 0.1550 | 3.13 | 0.1465 | 2.65 | 0.1254 | 2.88 |
| 10.451 | 0.1648 | 3.13 | 0.1542 | 3.07 | 0.1460 | 2.61 | 0.1251 | 2.84 |
| 10.950 | 0.1643 | 3.07 | 0.1533 | 3.03 | 0.1455 | 2.57 | 0.1246 | 2.80 |
| 11.445 | 0.1637 | 3.02 | 0.1527 | 2.98 | 0.1450 | 2.53 | 0.1240 | 2.76 |
| 11.943 | 0.1633 | 2.97 | 0.1520 | 2.93 | 0.1444 | 2.50 | 0.1235 | 2.72 |
| 12.441 | 0.1627 | 2.92 | 0.1512 | 2.89 | 0.1440 | 2.47 | 0.1230 | 2.69 |
| 12.940 | 0.1622 | 2.87 | 0.1505 | 2.85 | 0.1433 | 2.43 | 0.1224 | 2.66 |
| 13.437 | 0.1616 | 2.83 | 0.1497 | 2.81 | 0.1429 | 2.40 | 0.1220 | 2.63 |
| 13.936 | 0.1611 | 2.78 | 0.1493 | 2.77 | 0.1424 | 2.37 | 0.1214 | 2.59 |
| 14.435 | 0.1604 | 2.74 | 0.1485 | 2.74 | 0.1418 | 2.35 | 0.1209 | 2.57 |

TABLE 15b tan δ, strain sweep (60° C., 10 Hz), Examples 64-67

| Strain (%) | 64 (sample 52) | 65 (sample 53) | 66 (sample 54) | 67 (sample 55) |
|---|---|---|---|---|
| 0.249 | 0.1214 | 0.1169 | 0.1135 | 0.1012 |
| 0.497 | 0.1564 | 0.1460 | 0.1302 | 0.1063 |
| 0.746 | 0.1856 | 0.1724 | 0.1466 | 0.1140 |
| 0.995 | 0.2070 | 0.1921 | 0.1599 | 0.1214 |
| 1.243 | 0.2219 | 0.2057 | 0.1703 | 0.1275 |
| 1.492 | 0.2328 | 0.2154 | 0.1783 | 0.1330 |
| 1.741 | 0.2406 | 0.2223 | 0.1840 | 0.1377 |
| 1.988 | 0.2462 | 0.2270 | 0.1886 | 0.1411 |
| 2.238 | 0.2502 | 0.2302 | 0.1922 | 0.1442 |
| 2.486 | 0.2531 | 0.2322 | 0.1945 | 0.1467 |
| 2.737 | 0.2550 | 0.2335 | 0.1965 | 0.1487 |
| 2.984 | 0.2561 | 0.2341 | 0.1978 | 0.1501 |
| 3.234 | 0.2566 | 0.2341 | 0.1986 | 0.1514 |
| 3.481 | 0.2566 | 0.2336 | 0.1991 | 0.1525 |
| 3.732 | 0.2567 | 0.2330 | 0.1997 | 0.1530 |
| 3.978 | 0.2561 | 0.2320 | 0.1996 | 0.1537 |
| 4.230 | 0.2551 | 0.2309 | 0.1995 | 0.1540 |
| 4.477 | 0.2545 | 0.2298 | 0.1992 | 0.1545 |
| 4.728 | 0.2534 | 0.2285 | 0.1990 | 0.1544 |
| 4.975 | 0.2521 | 0.2273 | 0.1985 | 0.1545 |
| 5.474 | 0.2498 | 0.2244 | 0.1973 | 0.1543 |
| 5.970 | 0.2472 | 0.2218 | 0.1961 | 0.1539 |
| 6.469 | 0.2447 | 0.2190 | 0.1942 | 0.1533 |
| 6.967 | 0.2421 | 0.2161 | 0.1929 | 0.1527 |
| 7.464 | 0.2397 | 0.2136 | 0.1912 | 0.1518 |
| 7.964 | 0.2372 | 0.2112 | 0.1896 | 0.1512 |
| 8.462 | 0.2345 | 0.2087 | 0.1878 | 0.1501 |
| 8.961 | 0.2319 | 0.2064 | 0.1864 | 0.1491 |
| 9.460 | 0.2299 | 0.2043 | 0.1851 | 0.1483 |
| 9.958 | 0.2278 | 0.2022 | 0.1834 | 0.1475 |
| 10.452 | 0.2254 | 0.2004 | 0.1821 | 0.1467 |
| 10.950 | 0.2233 | 0.1985 | 0.1807 | 0.1460 |
| 11.449 | 0.2216 | 0.1968 | 0.1795 | 0.1451 |
| 11.948 | 0.2197 | 0.1949 | 0.1781 | 0.1442 |
| 12.445 | 0.2180 | 0.1935 | 0.1771 | 0.1435 |
| 12.942 | 0.2161 | 0.1918 | 0.1759 | 0.1427 |
| 13.441 | 0.2147 | 0.1906 | 0.1749 | 0.1420 |
| 13.939 | 0.2132 | 0.1892 | 0.1734 | 0.1413 |
| 14.438 | 0.2116 | 0.1879 | 0.1726 | 0.1407 |

TABLE 16a tan δ, temperature sweep (5% strain, 10 Hz), Examples 60-63

| Temp. (° C.) | 60 (sample 52) | 61 (sample 53) | 62 (sample 54) | 63 (sample 55) |
|---|---|---|---|---|
| −77.92 | 0.0168 | 0.0226 | 0.0206 | 0.0230 |
| −75.91 | 0.0165 | 0.0209 | 0.0195 | 0.0212 |
| −73.94 | 0.0166 | 0.0209 | 0.0191 | 0.0205 |
| −71.98 | 0.0171 | 0.0209 | 0.0190 | 0.0200 |
| −69.80 | 0.0179 | 0.0211 | 0.0194 | 0.0203 |
| −68.27 | 0.0189 | 0.0215 | 0.0205 | 0.0211 |
| −66.16 | 0.0210 | 0.0228 | 0.0223 | 0.0230 |
| −64.04 | 0.0241 | 0.0249 | 0.0253 | 0.0260 |
| −62.31 | 0.0291 | 0.0289 | 0.0305 | 0.0312 |
| −60.44 | 0.0368 | 0.0352 | 0.0379 | 0.0389 |
| −58.35 | 0.0467 | 0.0435 | 0.0473 | 0.0491 |
| −56.51 | 0.0578 | 0.0533 | 0.0575 | 0.0597 |
| −54.48 | 0.0680 | 0.0628 | 0.0653 | 0.0679 |
| −52.33 | 0.0743 | 0.0691 | 0.0687 | 0.0702 |
| −50.59 | 0.0768 | 0.0714 | 0.0682 | 0.0683 |
| −48.66 | 0.0766 | 0.0718 | 0.0668 | 0.0657 |
| −46.40 | 0.0759 | 0.0724 | 0.0663 | 0.0639 |
| −44.63 | 0.0761 | 0.0744 | 0.0675 | 0.0643 |
| −42.05 | 0.0782 | 0.0789 | 0.0714 | 0.0667 |
| −40.61 | 0.0819 | 0.0860 | 0.0776 | 0.0719 |
| −36.56 | 0.1021 | 0.1158 | 0.1035 | 0.0932 |
| −32.74 | 0.1559 | 0.1897 | 0.1642 | 0.1413 |
| −29.01 | 0.2822 | 0.3446 | 0.2897 | 0.2532 |
| −24.84 | 0.5075 | 0.5866 | 0.5075 | 0.4396 |
| −21.01 | 0.7268 | 0.7533 | 0.7246 | 0.6818 |
| −17.14 | 0.7282 | 0.6740 | 0.7437 | 0.7662 |
| −13.05 | 0.5616 | 0.4965 | 0.5906 | 0.6443 |
| −9.04 | 0.4140 | 0.3637 | 0.4416 | 0.4868 |
| 1.41 | 0.3629 | 0.3188 | 0.3772 | 0.3918 |
| 10.85 | 0.2587 | 0.2308 | 0.2658 | 0.2667 |
| 20.29 | 0.2102 | 0.1906 | 0.2134 | 0.2060 |
| 30.48 | 0.1857 | 0.1710 | 0.1838 | 0.1729 |
| 40.67 | 0.1693 | 0.1591 | 0.1659 | 0.1522 |
| 50.36 | 0.1567 | 0.1476 | 0.1503 | 0.1353 |
| 60.34 | 0.1470 | 0.1378 | 0.1388 | 0.1229 |
| 70.43 | 0.1386 | 0.1300 | 0.1302 | 0.1141 |
| 80.16 | 0.1304 | 0.1240 | 0.1219 | 0.1066 |
| 90.55 | 0.1240 | 0.1172 | 0.1149 | 0.1005 |
| 99.96 | 0.1174 | 0.1111 | 0.1097 | 0.0947 |

TABLE 16b tan δ, temperature sweep (5% strain, 10 Hz), Examples 64-67

| Temp. (° C.) | 64 (sample 52) | 65 (sample 53) | 66 (sample 54) | 67 (sample 55) |
|---|---|---|---|---|
| −78.11 | 0.0210 | 0.0204 | 0.0194 | 0.0180 |
| −75.94 | 0.0195 | 0.0189 | 0.0183 | 0.0168 |
| −73.97 | 0.0189 | 0.0181 | 0.0176 | 0.0163 |
| −71.98 | 0.0185 | 0.0176 | 0.0174 | 0.0158 |
| −69.72 | 0.0183 | 0.0173 | 0.0170 | 0.0156 |
| −67.90 | 0.0180 | 0.0172 | 0.0170 | 0.0155 |
| −66.24 | 0.0177 | 0.0169 | 0.0166 | 0.0154 |
| −64.22 | 0.0176 | 0.0170 | 0.0166 | 0.0156 |
| −62.13 | 0.0175 | 0.0170 | 0.0165 | 0.0157 |
| −60.44 | 0.0171 | 0.0166 | 0.0163 | 0.0158 |
| −58.48 | 0.0171 | 0.0167 | 0.0166 | 0.0158 |
| −56.46 | 0.0171 | 0.0168 | 0.0165 | 0.0160 |
| −54.62 | 0.0171 | 0.0170 | 0.0169 | 0.0164 |
| −52.44 | 0.0174 | 0.0176 | 0.0175 | 0.0168 |
| −50.59 | 0.0176 | 0.0182 | 0.0180 | 0.0174 |
| −48.63 | 0.0186 | 0.0191 | 0.0188 | 0.0182 |
| −46.66 | 0.0198 | 0.0206 | 0.0201 | 0.0193 |
| −44.53 | 0.0214 | 0.0226 | 0.0216 | 0.0211 |
| −42.57 | 0.0238 | 0.0258 | 0.0242 | 0.0231 |
| −40.73 | 0.0275 | 0.0311 | 0.0276 | 0.0271 |
| −36.61 | 0.0426 | 0.0531 | 0.0429 | 0.0412 |
| −32.98 | 0.0874 | 0.1185 | 0.0886 | 0.0827 |
| −29.09 | 0.2116 | 0.2851 | 0.2077 | 0.1959 |
| −25.18 | 0.4444 | 0.5528 | 0.4449 | 0.4308 |
| −21.02 | 0.7131 | 0.7745 | 0.7227 | 0.7256 |
| −17.23 | 0.7703 | 0.7406 | 0.7995 | 0.8779 |
| −13.28 | 0.6262 | 0.5718 | 0.6591 | 0.7666 |
| −8.94 | 0.4651 | 0.4271 | 0.4986 | 0.5920 |
| 0.95 | 0.4466 | 0.4094 | 0.4368 | 0.4673 |
| 10.71 | 0.3291 | 0.3040 | 0.3022 | 0.3057 |
| 20.10 | 0.2834 | 0.2632 | 0.2481 | 0.2354 |
| 30.07 | 0.2673 | 0.2496 | 0.2281 | 0.2090 |
| 40.23 | 0.2572 | 0.2416 | 0.2153 | 0.1944 |
| 50.22 | 0.2474 | 0.2341 | 0.2050 | 0.1828 |
| 60.07 | 0.2373 | 0.2256 | 0.1959 | 0.1741 |
| 69.92 | 0.2274 | 0.2164 | 0.1869 | 0.1649 |
| 79.85 | 0.2192 | 0.2098 | 0.1791 | 0.1565 |
| 89.87 | 0.2119 | 0.2033 | 0.1705 | 0.1484 |
| 99.96 | 0.2025 | 0.1949 | 0.1605 | 0.1402 |

The data of Tables 15a and 15b (strain sweep at 60° C.) show that, inter alia, the presence of B units results in a reduction of tan δ, indicative of reduced hysteresis. The data of Tables 16a and 16b show that the presence of B units results in a general increase in peak tan δ and tan δ at 0° C., indicative of, inter alia, improved cold and wet traction performance.

Example 68: Synthesis of 3,4,5-tri(tert-butyldimethylsiloxy)benzaldehyde

To a dried 250 mL flask including a magnetic stirring bar was added ~5.0 g 3,4,5-trihydroxybenzaldehyde, ~0.3 g DMAP, 60 mL THF, and 10 mL triethylamine, followed by syringe addition of a solution of ~15.2 g tert-butyldimethylsilyl chloride in 30 mL THF. This mixture was allowed to stir (under nitrogen) at room temperature for about an hour. Solid was filtered out of the mixture, and solvent was evaporated before the filtrate was purified using silica gel column chromatography employing 10% ethyl acetate in hexane as eluting solvent. A waxy product (15.3 g, 96% yield) was obtained. $^1$H and $^{13}$C NMR confirmed the compound to be 3,4,5-tri(tert-butyldimethylsiloxy)benzaldehyde.

Example 69: Synthesis of 3,4,5-tri(tert-butyldimethylsiloxy)styrene

To a stirred, cold (0° C.) solution of ~11.5 g MTP-Br in 100 mL dried THF under nitrogen was dropwise added ~19.5 mL n-BuLi solution. After ~10 minutes, a solution of 15.0 g of the product from Example 68 in 30 mL THF was dropwise added via syringe. The resulting yellow suspension was stirred for ~4 hours before being treated with NH$_4$Cl. This solution was filtered and concentrated under vacuum. The residue was purified by silica gel column chromatography using 5% ethyl acetate in hexane as the eluting solvent, resulting in collection of ~13.4 g (90% yield) of a colorless oil. $^1$H and $^{13}$C NMR confirmed the compound to be 3,4,5-tri(tert-butyldimethylsiloxy)styrene (TTBDMSOS).

Example 70: SBR (Control)

To a N$_2$-purged reactor equipped with a stirrer was added ~1.55 kg hexane, ~0.41 kg styrene solution, and ~2.52 kg butadiene solution (21.6% in hexane).

The reactor was charged with ~3.0 mL n-BuLi solution (1.7 M) followed by 1.10 mL 2,2-bis(2'-tetrahydrofuryl)propane solution. The reactor jacket was heated to 50° C. and, after ~34 minutes, the batch temperature peaked at ~63° C.

After an additional ~30 minutes, the polymer cement was dropped into isopropanol containing BHT and drum dried. This polymer is designated sample 70 in Table 17 below.

Examples 71-74: Interpolymers including 3,4,5-tri(tert-butyldimethylsiloxy)styrene Units A polymerization in a N$_2$-purged reactor similar to that from Example 70 was performed. Other than the amount of initiator solution (~2.9 mL here), the amounts of materials added were identical to those from Example 70. The reactor jacket was heated to 50° C. and, after ~35 minutes, the batch temperature peaked at ~64° C.

After ~30 additional minutes, 5 mL of a 1.0 M solution of the TTBDMSOS (1.0 M in hexane) was charged to the reactor; this mixture was stirred at 50° C. for ~30 minutes before portions of the polymer cement were transferred to glass bottles and terminated with sample 71—isopropanol,
sample 72—SnCl$_4$, 0.25 M in hexane (using a 1:1 ratio of Sn to Li),
sample 73—DMI, 1.0 M in toluene, and
sample 74—APMDEOS, 1.0 M in hexane.

Each sample was agitated for an additional ~30 minutes in a 50° C. water bath.

Half of sample 71 was transferred to another bottle, and this is designated sample 71a below.

The protecting groups from samples 71a and 73-74 were hydrolyzed by reaction at room temperature for ~60 minutes with TBAF solution (1M solution in THF containing ~5% water, using an amount so as to result in a TBAF-to-TTBDMSOS ratio of 11:10).

Each polymer cement was coagulated and dried as in Example 70.

TABLE 17

| Polymer properties | | | | | | |
|---|---|---|---|---|---|---|
| | 70 | 71 | 71a | 72 | 73 | 74 |
| $M_n$ (kg/mol) | 128 | 141 | 156 | 248 | 137 | 155 |
| $M_p$ (kg/mol) | 133 | 140 | 140 | 461 | 140 | 140 |
| $M_w/M_n$ | 1.03 | 1.07 | 1.21 | 1.46 | 1.63 | 1.22 |
| $T_g$ (° C.) | −37.7 | −36.1 | −36.1 | −36.8 | −37.2 | −36.7 |
| % coupling | 0.58 | 9.12 | 24.7 | 69.2 | 49.6 | 24.4 |

Example 75: Cold Flow Testing

The polymers of Examples 70 and 73-74, as well as DMI- and APMDEOS-terminated SBRs (i.e., no B units included in the polymer chain), were used to prepare test samples using the procedure set forth above.

The test results indicated that the samples prepared from the polymers of Examples 73-74 both were better (~2 mm thicker at any given temperature) than a sample prepared from a similar polymer which did not include B units.

Examples 76-87: Preparation and Testing of Vulcanizates

Using the formulations from Table 9a and 9b above, vulcanizable elastomeric compounds containing reinforcing fillers were prepared from samples 70-74. Those prepared from the Table 9a formulation are denominated Examples 76-81 respectively, while those prepared from the Table 9b formulation are denominated Examples 82-87 respectively. Vulcanizates were prepared by curing these compounds for ~15 minutes at 171° C.

Physical testing similar to that set forth above (i.e., tan δ versus both % strain (at 60° C.) and temperature, both at 10 Hz) showed that vulcanizates employing SBR interpolymers that designed to include one or more B mer adjacent terminal functionalities exhibit significant reductions in hysteresis and other desirable properties in both carbon black- and silica-containing vulcanizates.

A complete set of physical performance data was obtained and is summarized below in Tables 18 and 19.

TABLE 18

Compound and vulcanizate properties, silica compound

| | 76 | 77 | 78 | 79 | 80 | 81 |
|---|---|---|---|---|---|---|
| | \multicolumn{6}{c}{synthetic polymer (sample no.)} | | | | | |
| | 70 | 71 | 71a | 72 | 73 | 74 |
| MDR2000 @ 171° C. (final) | | | | | | |
| ML (kg · cm) | 1.81 | 2.06 | 2.26 | 3.05 | 2.51 | 2.60 |
| MH (kg · cm) | 23.11 | 24.50 | 23.63 | 24.36 | 22.72 | 21.90 |
| $t_{90}$ (min) | 7.52 | 6.64 | 5.00 | 6.51 | 5.29 | 5.29 |
| $ML_{1+4}$ @ 100° C. (final) | 19.4 | 23.7 | 34.7 | 44.3 | 47.3 | 47.3 |
| Tensile @ 23° C. (final, unaged) | | | | | | |
| $M_{50}$ (MPa) | 1.81 | 1.92 | 1.98 | 1.88 | 2.03 | 1.85 |
| $M_{200}$ (MPa) | 6.99 | 7.78 | 8.57 | 7.72 | 8.91 | 8.26 |
| $T_b$ (MPa) | 11.1 | 13.3 | 12.9 | 11.0 | 11.5 | 11.1 |
| $E_b$ (%) | 288 | 301 | 272 | 262 | 243 | 248 |
| Tensile @ 100° C. (final, unaged) | | | | | | |
| $M_{50}$ (MPa) | 1.67 | 1.86 | 1.93 | 1.85 | 2.04 | 1.86 |
| $M_{100}$ (MPa) | 3.00 | 3.39 | 3.67 | 3.41 | 3.91 | 3.57 |
| $T_b$ (MPa) | 6.3 | 5.9 | 7.1 | 5.9 | 5.9 | 6.8 |
| $E_b$ (%) | 204 | 169 | 184 | 170 | 150 | 180 |
| Strain sweep (60° C., 10 Hz, final) | | | | | | |
| G' @ 5% strain (MPa) | 3.913 | 4.027 | 3.358 | 3.583 | 3.076 | 3.031 |
| G" @ 5% strain (MPa) | 0.596 | 0.585 | 0.391 | 0.446 | 0.265 | 0.277 |
| tan δ | 0.1523 | 0.1451 | 0.1165 | 0.1246 | 0.0863 | 0.0913 |
| ΔG' (MPa) | 4.319 | 4.266 | 2.411 | 3.007 | 1.283 | 1.406 |
| Temp. sweep (2% strain, 10 Hz, final) | | | | | | |
| G' @ 0° C. (MPa) | 16.912 | 15.208 | 13.477 | 13.513 | 11.173 | 9.577 |
| G" @ 0° C. (MPa) | 5.545 | 4.951 | 4.729 | 4.642 | 4.154 | 3.629 |
| tan δ @ 0° C. (MPa) | 0.3256 | 0.3229 | 0.3477 | 0.3407 | 0.3678 | 0.3745 |
| G' @ 60° C. (MPa) | 8.275 | 7.698 | 6.552 | 6.612 | 5.577 | 4.768 |
| G" @ 60° C. (MPa) | 1.164 | 0.945 | 0.750 | 0.751 | 0.532 | 0.396 |
| tan δ @ 60° C. (MPa) | 0.1407 | 0.1227 | 0.1145 | 0.1136 | 0.0954 | 0.0831 |
| Dynastat (60° C., final) | | | | | | |
| tan δ | 0.1218 | 0.1162 | 0.0925 | 0.1022 | 0.0702 | 0.0727 |
| Bound rubber (%) | 19.6 | 20.8 | 30.0 | 28.0 | 34.9 | 47.3 |

TABLE 19

Compound and vulcanizate properties, carbon black compound

| | 82 | 83 | 84 | 85 | 86 | 87 |
|---|---|---|---|---|---|---|
| | \multicolumn{6}{c}{synthetic polymer (sample no.)} | | | | | |
| | 70 | 71 | 71a | 72 | 73 | 74 |
| MDR2000 @ 171° C. (final) | | | | | | |
| ML (kg · cm) | 0.88 | 1.07 | 1.31 | 1.70 | 1.82 | 1.67 |
| MH (kg · cm) | 17.14 | 17.13 | 17.32 | 16.24 | 15.93 | 16.66 |
| $t_{90}$ (min) | 6.80 | 7.39 | 9.28 | 7.02 | 9.19 | 8.47 |
| $ML_{1+4}$ @ 100° C. (final) | 23.0 | 29.3 | 41.5 | 49.7 | 55.3 | 50.9 |
| Tensile @ 23° C. (final, unaged) | | | | | | |
| $M_{50}$ (MPa) | 1.37 | 1.37 | 1.34 | 1.24 | 1.21 | 1.21 |
| $M_{300}$ (MPa) | 7.53 | 7.56 | 8.85 | 8.68 | 9.51 | 9.47 |
| $T_b$ (MPa) | 15.2 | 12.3 | 13.3 | 18.0 | 13.6 | 15.0 |
| $E_b$ (%) | 523 | 434 | 403 | 509 | 382 | 417 |
| Tensile @ 100° C. (final, unaged) | | | | | | |
| $M_{50}$ (MPa) | 1.06 | 1.07 | 1.13 | 1.11 | 1.10 | 1.10 |
| $M_{200}$ (MPa) | 3.97 | 3.96 | 4.59 | 4.52 | 4.94 | 4.91 |
| $T_b$ (MPa) | 8.0 | 8.5 | 6.5 | 7.9 | 5.2 | 7.8 |
| $E_b$ (%) | 347 | 363 | 288 | 295 | 209 | 273 |

TABLE 19-continued

| Compound and vulcanizate properties, carbon black compound | | | | | | |
|---|---|---|---|---|---|---|
| | 82 | 83 | 84 | 85 | 86 | 87 |
| | synthetic polymer (sample no.) | | | | | |
| | 70 | 71 | 71a | 72 | 73 | 74 |
| Strain sweep (60° C., 10 Hz, final) | | | | | | |
| G' @ 5% strain (MPa) | 3.017 | 2.954 | 2.592 | 2.435 | 2.428 | 2.466 |
| G" @ 5% strain (MPa) | 0.686 | 0.651 | 0.397 | 0.341 | 0.256 | 0.295 |
| tan δ | 0.2275 | 0.2202 | 0.1533 | 0.1400 | 0.1053 | 0.1197 |
| ΔG' (MPa) | 3.832 | 3.550 | 1.549 | 1.182 | 0.668 | 0.916 |
| Temp. sweep (2% strain, 10 Hz, final) | | | | | | |
| G' @ 0° C. (MPa) | 15.112 | 14.778 | 12.050 | 11.149 | 7.742 | 9.731 |
| G" @ 0° C. (MPa) | 5.989 | 6.272 | 5.042 | 4.927 | 3.489 | 4.251 |
| tan δ @ 0° C. (MPa) | 0.3960 | 0.4240 | 0.4177 | 0.4409 | 0.4505 | 0.4367 |
| G' @ 60° C. (MPa) | 5.288 | 4.978 | 4.552 | 4.004 | 3.048 | 3.798 |
| G" @ 60° C. (MPa) | 1.144 | 1.138 | 0.780 | 0.673 | 0.379 | 0.533 |
| tan δ @ 60° C. (MPa) | 0.2164 | 0.2286 | 0.1713 | 0.1682 | 0.1245 | 0.1402 |
| Dynastat (60° C., final) | | | | | | |
| tan δ | 0.2134 | 0.2072 | 0.1406 | 0.1386 | 0.1052 | 0.1168 |
| Bound rubber (%) | 11.9 | 12.3 | 22.7 | 28.1 | 37.1 | 32.2 |

That which is claimed is:

1. A compound useful for anionically initiating polymerization of ethylenically unsaturated monomers, said compound having the general formula

where
- M is an alkali metal atom;
- $R^1$ is a phenyl or polycyclic aromatic group having at least two $OR^2$ substituent groups, with each $R^2$ being a hydrolyzable protecting group which is nonreactive toward M;
- Z is a single bond or a substituted or unsubstituted acyclic alkylene, cyclic alkylene or arylene group; and
- Q is a group bonded to M through a N or Sn atom.

2. The compound of claim 1 wherein Q is $SnR^7_2$ where each $R^7$ independently is a hydrocarbyl group or together, with the Sn atom, form a cyclic group.

3. The compound of claim 1 wherein Q is $NR^8$ where $R^8$ is a hydrocarbyl group.

4. The compound of claim 1 wherein said $OR^2$ substituent groups are on adjacent ring C atoms of said phenyl or polycyclic aromatic group.

5. The compound of claim 4 wherein said $OR^2$ substituent groups are on adjacent ring C atoms of a phenyl group.

6. The compound of claim 1 wherein each $R^2$ is a t-butyldimethyl-siloxyl group.

* * * * *